United States Patent
Chaudhary

(10) Patent No.: US 12,415,987 B2
(45) Date of Patent: *Sep. 16, 2025

(54) METHODS AND COMPOSITION FOR PRODUCING AND USING IMMUNE CELLS AND STEM CELLS FOR CELL-BASED THERAPIES

(71) Applicant: Angeles Therapeutics, Inc., Toluca Lake, CA (US)

(72) Inventor: Preet M. Chaudhary, Toluca Lake, CA (US)

(73) Assignee: Angeles Therapeutics, Inc., Toluca Lake, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 17/861,534

(22) Filed: Jul. 11, 2022

(65) Prior Publication Data

US 2022/0387502 A1   Dec. 8, 2022

Related U.S. Application Data

(63) Continuation of application No. 16/315,153, filed as application No. PCT/US2017/042248 on Jul. 14, 2017, now Pat. No. 11,382,931.

(60) Provisional application No. 62/362,497, filed on Jul. 14, 2016.

(51) Int. Cl.
| | |
|---|---|
| C12N 5/0783 | (2010.01) |
| A61K 40/11 | (2025.01) |
| A61K 40/22 | (2025.01) |
| A61K 40/31 | (2025.01) |
| A61K 40/41 | (2025.01) |
| A61K 40/42 | (2025.01) |
| A61K 40/46 | (2025.01) |
| A61P 31/18 | (2006.01) |
| A61P 35/00 | (2006.01) |
| A61P 37/06 | (2006.01) |
| C12N 5/0781 | (2010.01) |
| C12N 5/0789 | (2010.01) |
| A61K 40/50 | (2025.01) |

(52) U.S. Cl.
CPC ............ *C12N 5/0636* (2013.01); *A61K 40/11* (2025.01); *A61K 40/22* (2025.01); *A61K 40/31* (2025.01); *A61K 40/418* (2025.01); *A61K 40/42* (2025.01); *A61K 40/421* (2025.01); *A61K 40/4211* (2025.01); *A61K 40/46* (2025.01); *A61P 31/18* (2018.01); *A61P 35/00* (2018.01); *A61P 37/06* (2018.01); *C12N 5/0635* (2013.01); *C12N 5/0646* (2013.01); *C12N 5/0647* (2013.01); *A61K 40/50* (2025.01); *A61K 2239/31* (2023.05); *A61K 2239/38* (2023.05); *A61K 2239/48* (2023.05); *C12N 2503/02* (2013.01); *C12N 2523/00* (2013.01); *C12N 2529/10* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,464,753 | A  | 11/1995 | Chaudhary |
| 5,945,337 | A  | 8/1999  | Brown et al. |
| 8,507,273 | B2 | 8/2013  | Frank |
| 2005/0266557 | A1 | 12/2005 | Proulx et al. |
| 2006/0088507 | A1 | 4/2006  | Roy et al. |
| 2009/0298045 | A1 | 12/2009 | Treves et al. |

FOREIGN PATENT DOCUMENTS

WO       1998/13072 A1    4/1998

OTHER PUBLICATIONS

Chang et al. Cellular Immunology, 1997, v.176, pp. 135-145).*
Pendsea et al., "P-glycoprotein and alloimmune T-cell activation", Clin Appl Immunol Rev., vol. 4, No. 1, 12 pages, Jul. 2003.
Bayer, Martin, Search Report, Application No. 17828580.5, European Patent Office, Feb. 20, 2020.
Chaudhary P M et al., "Expression and activity of P-glycoprotein, a multidrug efflux pump, in human hematopoietic stem cells", Cell, vol. 66, No. 1, Jul. 12, 1991, pp. 85-94.
Ward et al., "Retroviral transfer and expression of the human multiple drug resistance (MDR) gene in peripheral blood progenitor cells," Clin Cancer Res., vol. 2, No. 5, pp. 873-876, May 1996.
Copenheaver, Blaine R., International Search Report and Written Opinion, U.S. Patent & Trademark Office, PCT/US2017/042248, Oct. 2, 2017.
D'Alessio, F. et al., "Polychromatic flow cytometry analysis of CD34+ hematopoietic stem cells in cryopreserved early preterm human cord blood samples", Cytometry Part A, vol. 79A, No. 1, Nov. 10, 2010, pp. 14-24.
Guimond et al., "P-glycoprotein targeting: a unique strategy to selectively eliminate immunoreactive T cells," Blood, vol. 100, No. 2, pp. 375-382, Jul. 2002.
Guo et al., "Chemoprotection effect of retroviral vector encoding multidrug resistance 1 gene to allow intensified chemotherapy in vivo," Cancer Chemother. Pharmacol., vol. 58, No. 1, pp. 40-49, Nov. 2005.
McIver, Zachariah A. et al., "Selective photodepletion of malignant T cells in extracorporeal photopheresis with selenorhodamine photosensitizers", Bioroganic & Medicinal Chemistry, vol. 24, No. 17, Jun. 2, 2016, pp. 3918-3931.

(Continued)

*Primary Examiner* — Michail A Belyavskyi
(74) *Attorney, Agent, or Firm* — IPath, PLC; Steven J. Miller

(57) ABSTRACT

Described herein are methods for selecting lymphocytes for adoptive cell therapy based on P-glycoprotein expression and compositions comprising same.

11 Claims, 8 Drawing Sheets

Specification includes a Sequence Listing.

(56) References Cited

OTHER PUBLICATIONS

Perruccio et al., "Photodynamic purging of alloreactive T cells for adoptive immunotherapy after haploidentical stem cell transplantation", Blood Cells, Molecules and Diseases, vol. 40, No. 1, Nov. 5, 2007, pp. 76-83.
Wittmann-Regis, Agnes, International Preliminary Report on Patentability and Written Opinion, The International Bureau of WIPO, PCT/US2017/042248, Jan. 24, 2019.

* cited by examiner

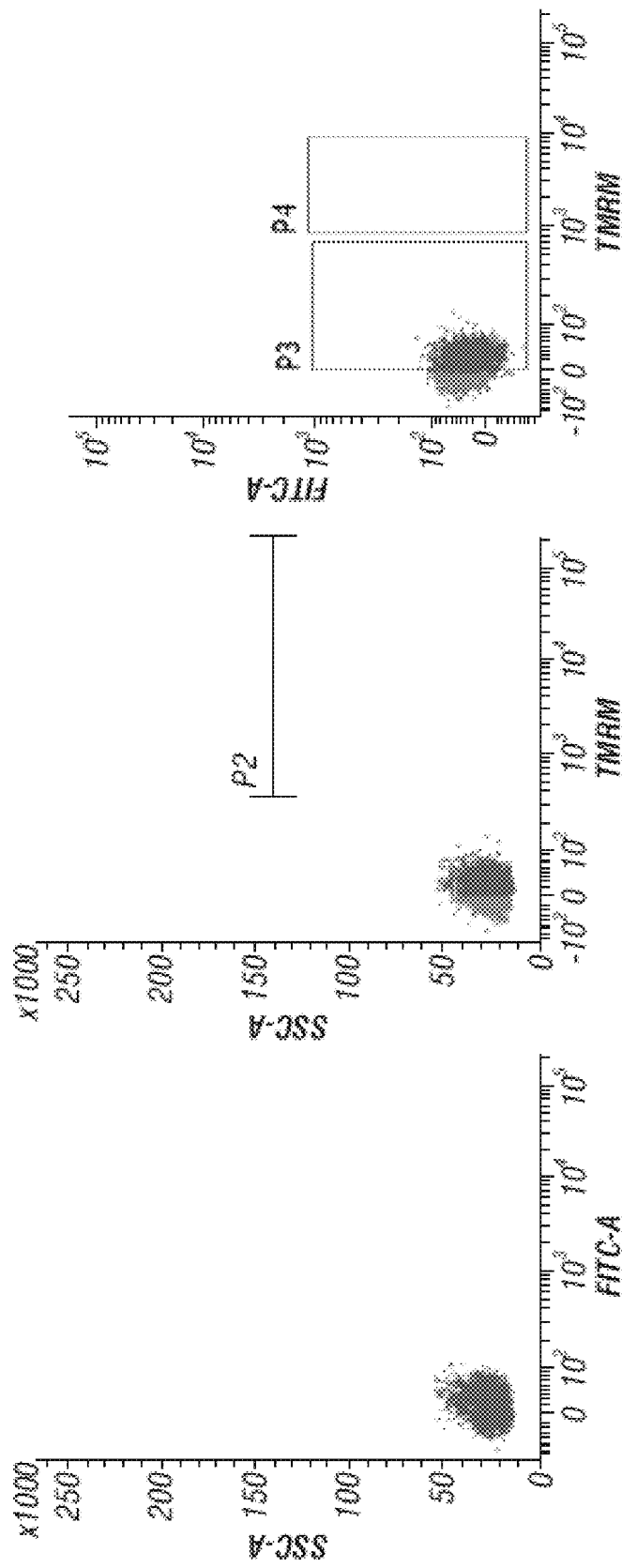

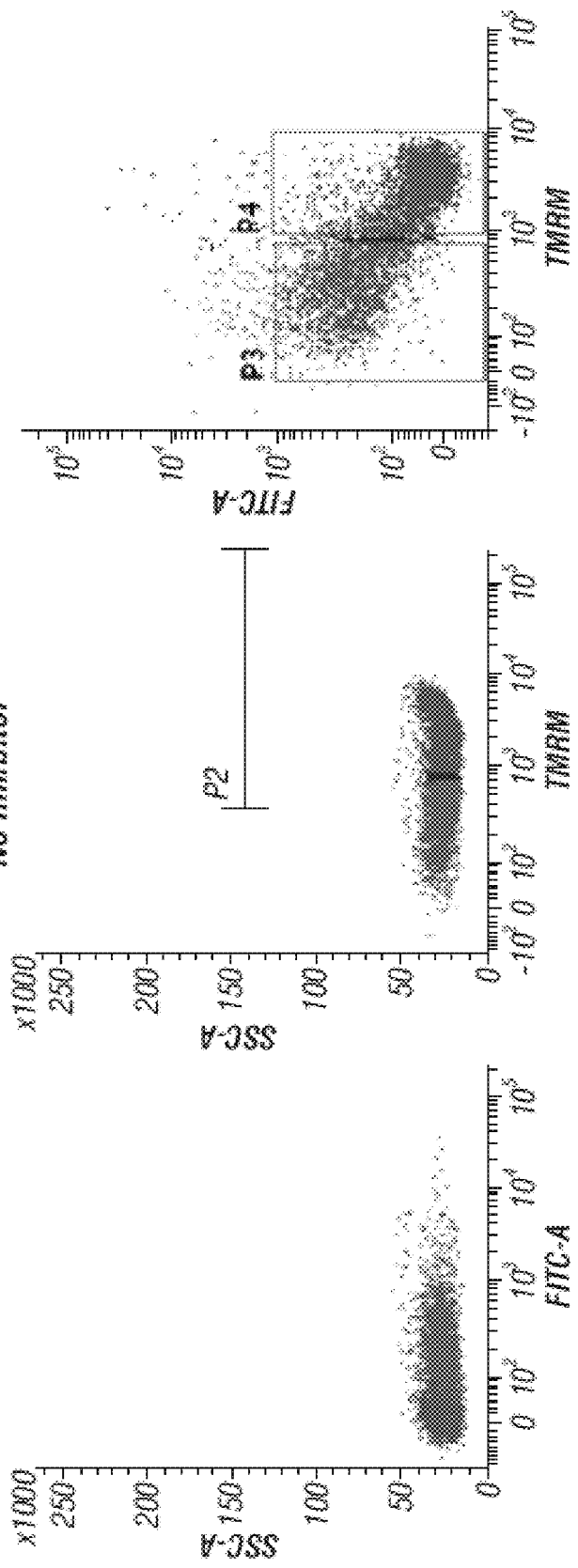

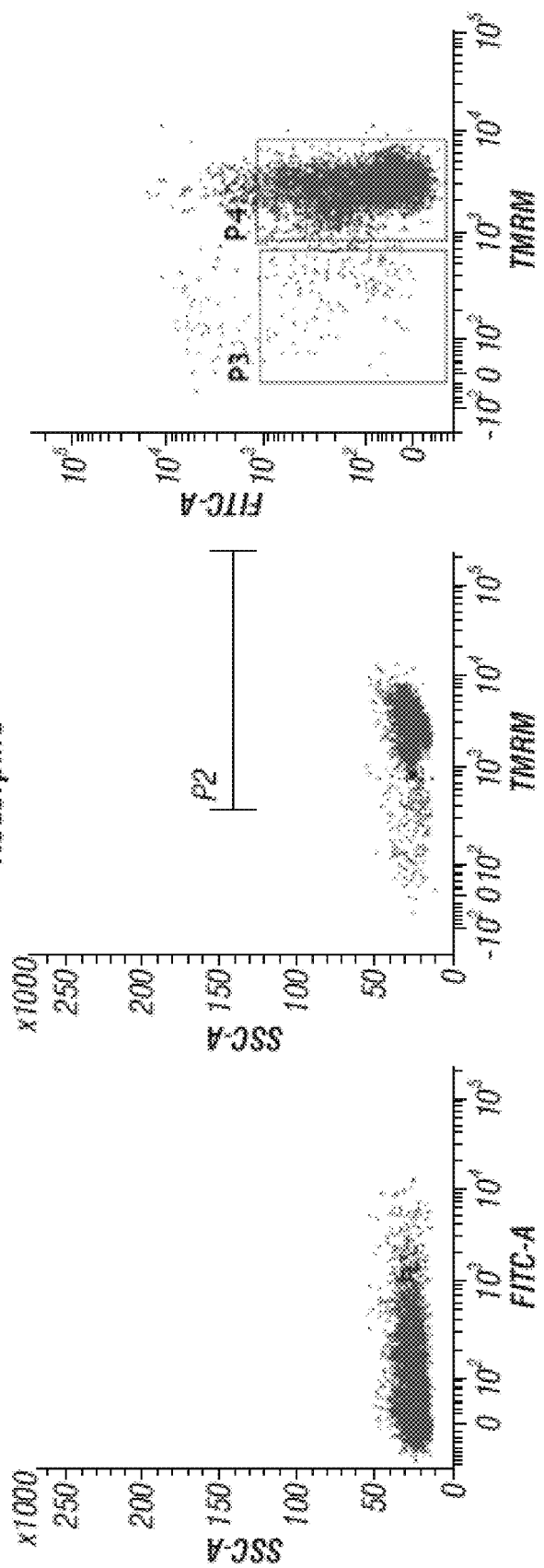

METHODS AND COMPOSITION FOR PRODUCING AND USING IMMUNE CELLS AND STEM CELLS FOR CELL-BASED THERAPIES

CROSS REFERENCE TO RELATED APPLICATIONS

The application is a continuation of U.S. application Ser. No. 16/315,153, now U.S. Pat. No. 11,382,931, filed Jan. 3, 2019, which application is a U.S. National Stage Application filed under 35 U.S.C. § 371 and claims priority to International Application No. PCT/US2017/042248, filed Jul. 14, 2017, which application claims priority under 35 U.S.C. § 119 to U.S. Provisional Application Ser. No. 62/362,497, filed Jul. 14, 2016, the disclosures of which are incorporated herein by reference.

TECHNICAL FIELD

Provided herein are methods for selecting lymphocytes for adoptive cell therapy based and methods of using such lymphocytes.

INCORPORATION BY REFERENCE OF SEQUENCE LISTING

This application includes a sequence listing entitled, "00130-010US2.xml" created on Aug. 2, 2022 and having 11,692 bytes of data, machine formatted on IBM-PC, MS-Windows operating system using WIPO Standard ST.26 formatting. The sequence listing is hereby incorporated by reference in its entirety for all purposes.

BACKGROUND

Immunotherapy using adoptive transfer of tumor-specific T cells and chimeric antigen receptor (CAR) and T cell receptor (TCR) modified T cells mediates durable and complete disease regression in some patients with metastatic cancer. Recent studies have suggested that metabolism supports and drives many basic features of T cells, including cellular activation, proliferation, differentiation, effector function, and antitumor immunity. This has led to a growing interest in leveraging this understanding to improve the efficacy of T cell transfer therapies, such as adoptive transfer immunotherapy in the treatment of cancer.

Although there is increasing evidence that metabolism can affect the survival and antitumor function of T cells, identifying a simple and clinically feasible method to isolate T cells with favorable metabolic features has proved challenging. Because mitochondria are the central metabolic organelle in cells, Sukumar et al. (Cell Metabolism, 23:63-76, 2016) hypothesized that the measurement of a single mitochondrial-associated parameter may help to identify T cells with a favorable bioenergetic profile that can survive in vivo for long periods after adoptive transfer for T cell-based immunotherapy, such as CAR-T, TCR and chimeric T cell receptor (cTCR) based therapies.

Sukumar et al. described a clinically feasible method to isolate functionally robust T cells based on a single metabolic parameter: mitochondrial membrane potential ($\Delta\Psi m$). Mitochondria produce energy by establishing an electrochemical proton motive force ($\Delta p$) across their inner cell membrane, which in turn fuels the synthesis of ATP by driving the proton turbine F0F1 ATPase. Sukumar et al. utilized a lipophilic cationic dye tetramethylrhodamine methyl ester (TMRM) to identify and isolate metabolically robust T cells based on their mitochondrial membrane potential ($\Delta\Psi m$). They showed that CD8+ T cells that are found to have low-$\Delta\Psi m$ display enhanced in vivo persistence and greater antitumor immunity relative to high-$\Delta\Psi m$ cells. Based on these findings, the authors claimed that they have demonstrated that metabolic sorting can complement sorting based on conventional cell surface markers in identifying cells with the capacity for long-term survival and ongoing effector function after adoptive transfer. They further believed that immunometabolomic approach to cell sorting may have important and immediate therapeutic applications in enhancing cell-based therapies for patients with viral-associated illness, advanced cancer, and disorders of hematopoiesis. However, sorting of lymphocytes based on TMRM staining and flow sorting is slow and expensive and therefore not readily amenable to clinical application.

SUMMARY

The disclosure provides a method for isolating cells suitable for adoptive cell therapy. The method comprises isolating p-glycoprotein (Pgp) positive cells. The disclosure provides a method for isolating cells suitable for adoptive cell therapy. The method comprises obtaining a sample; optionally enriching the sample for T cells, NK cells, stem cells, and/or mononuclear cells; and isolating p-glycoprotein positive (Pgp-positive) including cells selected from the group consisting of T cells, NK cells, stem cells, and/or mononuclear cells from the enriched sample, so as to obtain a fraction enriched in Pgp-positive cells, thereby isolating cells suitable for adoptive cell transfer therapy. In a further embodiment, the method comprises contacting the sample with at least one cytotoxic drug that is a substrate of Pgp at a concentration appropriate to kill Pgp-negative T cells, NK cells and/or differentiated cells. In further embodiment, the at least one cytotoxic drug is any one or more of vincristine, vinblastin, doxorubicin, daunorubicin, taxol, paclitaxol, etoposide, mitoxantrone, actinomycin-D, or combinations thereof. In still a further embodiment or alternative embodiment, the method comprises contacting the sample with at least one phototoxic compound; and exposing the sample to a visible light source sufficient to activate the at least one phototoxic compound so as to kill Pgp-negative T cells. In a further embodiment, the at least one phototoxic compound is any one or more of 2-(4,5-dibromo-6-amino-3-imino-3H-xanthen-9-yl)-benzoic acid methyl ester hydrochloride, 2-(4,5-dibromo-6-amino-3-imino-3H-xanthen-9-yl)-benzoic acid ethyl ester hydrochloride, 2-(4,5-dibromo-6-amino-3-imino-3H-xanthen-9-yl)-benzoic acid octyl ester hydrochloride, 2-(4,5-dibromo-6-amino-3-imino-3H-xanthen-9-yl)-benzoic acid n-butyl ester hydrochloride, 2-(6-ethyl amino-3-ethyl imino-3H-xanthen-9-yl)-benzoic acid n-butyl ester hydrochloride, or derivatives thereof or combinations thereof. In yet another or further embodiment, the method comprises exposing the sample to a physical stress, such as hyperthermic conditions, that selectively kills Pgp-negative cells. In yet another or further embodiment, the method comprises exposing the sample to a nutritional or metabolic stress, such as serum starvation or growth factor starvation, which selectively kills pgp-negative cells. In still another or alternative embodiment of any of the foregoing the method includes isolating the Pgp-positive cells from the sample by exposing the sample to at least one primary antibody or antibody-like moiety specific to p-glycoprotein. In a further embodiment, the at least one primary antibody or antibody like moiety is conjugated to at least one fluorescent label or at least one magnetic label or biotin. In still a further embodiment, the method includes optionally staining the sample with at least one secondary antibody. In a further embodiment, the at least one secondary antibody is conjugated to at least one fluorescent label or at least one magnetic label or biotin. In still another embodiment of any of the foregoing, the isolating of the Pgp-positive cells from the sample is performed by any one or more methods selected from immunofluorescent methods, immunomagnetic methods, immunoaffinity methods, or combinations thereof. In still another embodiment of any of the foregoing, the isolating of the Pgp-positive cells from the sample is performed by any one or more methods selected from flow cytometry, magnetic activated cell sorting, biotin-streptavidin affinity purification, or combinations thereof. In still another embodiment of any of the foregoing, the fraction enriched in Pgp-positive cells contains less than 50%, less than 40%, less than 30%, less than 20%, less than 10%, less than 5%, or less than 1% Pgp-negative cells. In yet a further embodiment, the disclosure provides tha the Pgp-positive cells are genetically modified. In yet a further embodiment, the disclosure provides that the Pgp-positive T cells, NK cells, stem cells, and/or mononuclear cells are further genetically modified to express at least one chimeric antigen receptor, T cell receptor, chimeric T cell receptor, synthetic immune receptor, TRuC™ or Artemis™ T cell platform, so as to obtain genetically modified Pgp-positive T cells, NK cells, stem cells, and/or mononuclear cells.

The disclosure also provides pharmaceutical compositions comprising the Pgp-positive T cells and/or NK cells and/or stem cells of the disclosure and at least one pharmaceutically acceptable carrier. The disclosure also provides pharmaceutical compositions comprising the genetically modified Pgp-positive T cells and/or NK cells and/or stem cells and at least one pharmaceutically acceptable carrier. The pharmaceutical compositions can be administered to a human or other subject to treat cancer, immune disorders, or infections.

The disclosure also provides a method for treating cancer, immune or infectious disorders in a subject, comprising administering a therapeutically effective amount of a composition of the disclosure comprising a Pgp-positive T cells and/or NK cells or genetically engineered population thereof to the subject so as to treat cancer, immune or infectious disorders. In one embodiment, the cancer is B-cell lymphomas, T cell lymphomas, myeloma, myelodysplastic syndrome, skin cancer, brain tumor, breast cancer, colon cancer, rectal cancer, esophageal cancer, anal cancer, cancer of unknown primary site, endocrine cancer, testicular cancer, lung cancer, hepatocellular cancer, gastric cancer, pancreatic cancer, cervical cancer, ovarian cancer, liver cancer, bladder cancer, cancer of the urinary tract, cancer of reproductive organs, thyroid cancer, renal cancer, carcinoma, melanoma, head and neck cancer, brain cancer, prostate cancer, or leukemia. In another embodiment, the method further comprises administering a chemotherapeutic agent. In still another embodiment, the chemotherapeutic agent is selected from alkylating agents, alkyl sulfonates, aziridines, ethylenimines, methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, nitrosureas, antibiotics, dynemicin, bisphosphonates, an esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin, deoxydoxorubicin, epirubicin, esorubicin, idarubicin, marcellomycin, mitomycins, antimetabolites, folic acid analogues, purine analogs, pyrimidine analogs, androgens, anti-adrenals, folic acid replenisher, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, sizofuran, spirogermanium, tenuazonic acid, triaziquone, 2,2',2"-trichlorotriethylamine, trichothecenes, urethane, vindesine, dacarbazine, mannomustine, mitobronitol, mitolactol, pipobroman, gacytosine, arabinoside, cyclophosphamide, thiotepa, taxoids, chloranbucil, 6-thioguanine, mercaptopurine, methotrexate, platinum analogs, vinblastine, platinum, etoposide (VP-16), ifosfamide, mitoxantrone, vincristine, vinorelbine, novantrone, teniposide, edatrexate, daunomycin, aminopterin, xeloda, ibandronate, irinotecan, topoisomerase inhibitor RFS 2000; difluoromethylornithine, retinoids, capecitabine, combretastatin, leucovorin, oxaliplatin, lapatinib, inhibitors of PKC-alpha, Raf, H-Ras, EGFR and VEGF-A, tyrosine kinase inhibitors, nucleoside analogs, mTOR inhibitors, Bcl2-family inhibitors, immunomodulatory drugs and proteasome inhibitors that reduce cell proliferation, and pharmaceutically acceptable salts, acids or derivatives of any of the above, or combinations thereof. In a further embodiment, the composition and the chemotherapeutic agent are administered sequentially or simultaneously. In another embodiment, the method further comprises administering an anticancer agent, such as an antibody, antibody drug conjugate, bispecific antibody, DART, a single domain antibody, or a non-immunoglobulin antigen binding scaffold. In another embodiment, the method further comprises performing stem cell transplant. In another embodiment, the method further comprises administering an anti-infective agent. In another embodiment, the method further comprises administering an immunosuppressive agent.

The disclosure also provides a method for isolating Pgp-negative T cells, NK cells, and/or mononuclear cells suitable for adoptive cell transfer therapy, comprising obtaining a sample; optionally enriching the sample for T cells, NK cells, and/or mononuclear cells; and depleting Pgp-positive cells from the sample, so as to obtain a fraction enriched in Pgp-negative cells suitable for adoptive cell transfer therapy. In one embodiment, the method comprises depleting the Pgp-positive cells from the sample by exposing the sample to at least one primary antibody or antibody like moiety specific to p-glycoprotein. In a further embodiment, the at least one primary antibody or antibody like moiety is conjugated to at least one fluorescent label or at least one magnetic label or biotin. The method optionally can include staining the sample with at least one secondary antibody. In another embodiment, the at least one secondary antibody is conjugated to at least one fluorescent label or at least one magnetic label or biotin. In still another embodiment, the depleting of the Pgp-positive cells from the sample is performed by any one or more methods selected from immunofluorescent methods, immunomagnetic methods, or immunoaffinity methods, or combinations thereof. In yet another embodiment, the depleting of the Pgp-positive cells from the sample is performed by flow cytometry, magnetic activated cell sorting, or biotin-streptavidin based cell sorting, or combinations thereof. In a further embodiment of any of the foregoing, the fraction enriched in Pgp-negative T cells, NK cells, and/or mononuclear cells contains less than 50%, less than 40%, less than 30%, less than 20%, less than 10%, less than 5%, or less than 1% Pgp-positive cells.

The disclosure also provides a pharmaceutical composition, comprising an amount of the fraction enriched in Pgp-negative lymphocytes, T cells or NK cells and at least one pharmaceutically acceptable carrier.

The disclosure also provides a method of treating an infection in an immunodeficient HIV/AIDS subject, comprising administering a therapeutically effective amount of the composition comprising the fraction enriched in Pgp-negative T cells and/or NK cells to the subject so as to treat the infection. In one embodiment, the infection is caused by a viral, bacterial, fungal or protozoan pathogen. In a further embodiment, the infection is caused by cytomegalovirus, adenovirus, adeno-associated virus, BK virus, Human Herpesvirus 6, Human Herpesvirus 8, Epstein Barr virus, influenza virus, parainfluenza virus, measles virus, mumps virus, rhino virus, varicella virus, herpes simplex virus 1 and 2, HIV-1, HTLV1, mycobacterium tuberculosis, atypical mycobacteria species, toxoplasmosis, nocardia, aspergillus, mucor, or candida.

The disclosure also provides a method for reducing graft-versus-host disease in a subject undergoing an allogeneic stem cell transplant, comprising administering a therapeutically effective amount of the composition comprising the fraction enriched in Pgp-negative T cells and/or NK cells to the subject so as to reduce graft-versus-host disease.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A-L shows immunofluorescence staining and sorting to enrich for Pgp expression cells.

DETAILED DESCRIPTION

Figures 1J, 1K, 1L:
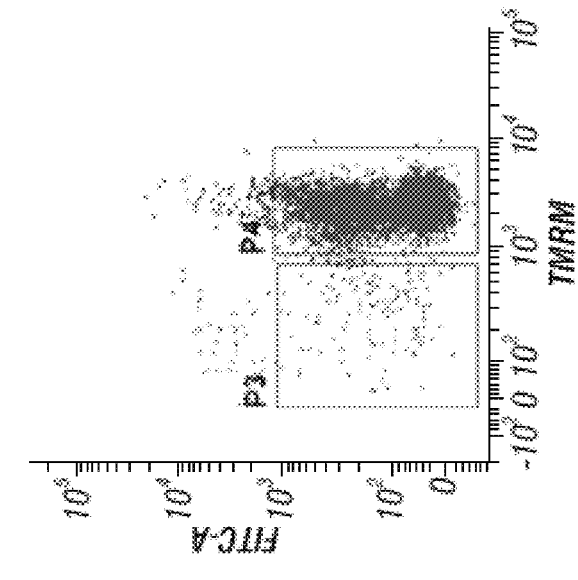

As used herein and in the appended claims, the singular forms "a," "and," and "the" include plural referents unless the context clearly dictates otherwise. Thus, for example, reference to "a cell" includes a plurality of such cells and reference to "the polynucleotide" includes reference to one or more polynucleotides and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless otherwise defined, all technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7 All headings and subheading provided herein are solely for ease of reading and should not be construed to limit the invention. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and specific examples are illustrative only and not intended to be limiting.

As used herein "beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), T cell lymphomas, myeloma, myelodysplastic syndrome, skin cancer, brain tumor, breast cancer, colon cancer, rectal cancer, esophageal cancer, anal cancer, cancer of unknown primary site, endocrine cancer, testicular cancer, lung cancer, hepatocellular cancer, gastric cancer, pancreatic cancer, cervical cancer, ovarian cancer, liver cancer, bladder cancer, cancer of the urinary tract, cancer of reproductive organs thyroid cancer, renal cancer, carcinoma, melanoma, head and neck cancer, brain cancer (e.g., glioblastoma multiforme), prostate cancer, including but not limited to androgen-dependent prostate cancer and androgen-independent prostate cancer, and leukemia. Other cancer and cell proliferative disorders will be readily recognized in the art.

"Chemotherapeutic agents" are compounds that are known to be of use in chemotherapy for cancer. Non-limiting examples of chemotherapeutic agents can include alkylating agents such as thiotepa and CYTOXAN☐ cyclosphosphamide; alkyl sulfonates such as busulfan, improsulfan and piposulfan; aziridines such as benzodopa, carboquone, meturedopa, and uredopa; ethylenimines and methylamelamines including altretamine, trietylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE; vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above or combinations thereof.

"Chimeric antigen receptors" (CAR) are artificial T cell receptors typically used as a therapy for cancer, using a technique called adoptive cell transfer. The essential antigen-binding, signaling, and stimulatory functions of the TCR complex have been reduced by genetic recombination methods to a single polypeptide chain, generally referred to as a Chimeric Antigen Receptor (CAR). See, e.g., Eshhar, U.S. Pat. No. 7,741,465; Eshhar, U.S. Patent Application Publication No. 2012/0093842. CARs are constructed specifically to stimulate T cell activation and proliferation in response to a specific antigen to which the CAR binds. Typically "CAR-T cells" are used, which refer to T-cells that have been engineered to containing a chimeric antigen receptor. Thus, T lymphocytes bearing such CARs are generally referred to as CAR-T lymphocytes. As described more fully, below, the disclosure provides for the isolation as well as isolated Pgp-positive cells that can be or are modified so that they express receptors that recognize proteins that are specific to the particular form of cancer. Such cells can be reintroduced to a subject, wherein the cells recognize and kill cancer cells. CARs have also been used for adoptive cell therapy of immune and infectious diseases. In addition to CAR, native, engineered and chimeric T cell receptors (TCR) have also been used for adoptive cell therapy.

"Disease targeted by genetically modified cells" as used herein encompasses the targeting of any cell involved in any manner in any disease by a genetically modified cells the hones to the disease or a target tissue or cell type, irrespective of whether the genetically modified cells target diseased cells or healthy cells to effectuate a therapeutically beneficial result.

"Genetically modified cells", "redirected cells", "genetically engineered cells" or "modified cells" as used herein refer to cells that have been modified to express a CAR and native, engineered or chimeric TCR. For example, a genetically modified T-lymphocyte that expresses a CAR is a genetically modified cell (sometimes referred to as a CAR-T cell).

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"P-glycoprotein" (P-gp or Pgp) is an ATP-dependent efflux pump with broad substrate specificity that pumps many foreign substances out of cells. P-glycoprotein is also known as multidrug resistance protein 1 (MDR1) or ATP-binding cassette sub-family B member 1 (ABCB1) or cluster of differentiation 243 (CD243). As used herein and as understood by one of skill in the art, Pgp-positive is abbreviated (Pgp$^+$) and Pgp-negative is abbreviated (Pgp$^-$).

"Stem cells" are cells capable of differentiation into other cell types and/or which retain the ability to continually replicate. Stem cells include those having a particular, specialized function (e.g., tissue specific cells, parenchymal cells and progenitors thereof). Progenitor cells (i.e., "multipotent") are cells that can give rise to different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism. As will be appreciated, "multipotent" stem/progenitor cells have a more narrow differentiation potential than do pluripotent stem cells. Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans). Moreover, in the case of lymphocytes a "stem cell lymphocyte" or "lymphocyte progenitor" can be a lymphocyte that has not been "activated" to target a particular antigen. Such lymphocyte progenitors retain the ability to be "activated" to target a particular antigen. Such lymphocyte progenitor cells are particularly useful in generating CAR-T cells as the progenitors can be readily targeted using a recombinant CAR and have greater replicative potential. Stem cells and progenitor cells of the disclosure include CD34$^+$ cells. The term "pluripotent hematopoietic stem cell" refers to a hematopoietic stem cell that can give rise to all blood cell types.

"Target cell" as used herein refers to cells which are involved in a disease and can be targeted to prevent or treat a disease condition by genetically modified cells of the disclosure (including but not limited to genetically modified T-cells, NK cells, hematopoietic stem cells, pluripotent stem cells, and embryonic stem cells). Other target cells will be apparent to those of skill in the art and may be used in connection with alternate embodiments of the disclosure.

The terms "T-cell" and "T-lymphocyte" are interchangeable and used synonymously herein. Examples include but are not limited to naïve T cells ("lymphocyte progenitors"), central memory T cells, effector memory T cells, stem memory T cells ($T_{scm}$) or combinations thereof.

Pgp positive lymphocytes of the disclosure include the following:
(1) T cells—(a) Pgp$^+$ T cells and subsets as defined by one or more immunological markers, such as CD8$^+$, CD4$^+$, CD62L$^+$, CCR7$^+$ etc.; (b) Pgp$^+$ T cells can also include different stages of differentiation, such as naïve T cells ("lymphocyte progenitors"), central memory T cells, effector memory T cells, memory stem T cells ($T_{SCM}$) etc.; (c) Pgp$^+$ T cells can also include different functional subclasses, such as Helper T cells, Cytotoxic T cells, Natural Killer T cells or regulatory T cells etc.; and (d) Pgp$^+$ T cells can also be classified based on the site from which they are obtained, such as peripheral blood, lymph nodes, spleen, bone marrow, tissue resident lymphocytes, tumor infiltrating lymphocytes etc.; and (2) NK Cells (Natural Killer cells)—(a) Pgp$^+$ NK cells and subsets as defined by one or more immunological markers, such as CD56hi, CD56lo etc.; (b) Pgp$^+$ NK cells can also include NK cells at different stages of differentiation, such as naïve NK cells etc.; (c) Pgp$^+$ NK cells can also be classified based on the site from which they are obtained, such as peripheral blood, lymph nodes, spleen, bone marrow, tissue resident lymphocytes, tumor infiltrating lymphocytes etc.

Pgp negative lymphocytes (e.g., for use in patients undergoing allogeneic stem cell transplantation to reduce the incidence of GVHD) include the following subsets:
(1) T cells—(a) Pgp$^-$ T cells and subsets as defined by one or more immunological markers, such as CD8$^+$, CD4$^+$, CD62L, CCR7 etc.; (b) Pgp$^-$ T cells can also include T cells at different stages of differentiation, such as naïve T cells ("lymphocyte progenitors"), central memory T cells, effector memory T cells, memory stem T cells (TSCM) etc.; (c) Pgp$^-$ T cells can also include cells belonging to different functional subclasses, such as Helper T cells, Cytotoxic T cells, Natural Killer T cells or regulatory T cells etc.; and (d) Pgp$^-$ T cells can also be classified based on the site from which they are obtained, such as peripheral blood, lymph nodes, spleen, bone marrow, tissue resident lymphocytes, tumor infiltrating lymphocytes etc.

The disclosure also covers methods to isolate hematopoietic stem cells for cellular and gene therapy applications using method that include one or more of (1) physical stress (e.g., hyperthermia), (2) nutritional and/or metabolic stress including, but not limited to, serum starvation and/or growth factor starvation; (3) chemical (e.g., exposure to chemotoxic compounds); and (4) exposure to Pgp-transported photo-toxic compounds.

The disclosure also demonstrates that Pgp expression correlates with the degree of stem-ness of a T or NK cell so that the cells with the highest level of Pgp expression are likely to be the most primitive (or most stem like).

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Tumor," as used herein refers to all neoplastic cell growth and proliferation, whether malignant or benign, and all pre-cancerous and cancerous cells and tissues.

As mentioned Sukumar et al. taught that robust lymphocyte were identifiable based on low mitochondrial membrane potential. In contrast, the present disclosure provides methods and compositions to identify robust lymphocyte cells using markers and methods that are easier and clinically feasible. The disclosure demonstrates that P-glycoprotein (P-gp or Pgp) expression is a strong indicator of lymphocyte differentiation and biological activity. Moreover, the disclosure provides various dyes, chemotherapeutic agents, nutritional and/or metabolic and physical stresses useful for selecting robust lymphocyte cell types.

The cells and methods described herein use, in some cases, one or more markers wherein at least one marker is Pgp. A molecule is a "marker" of a desired cell type if it is found on a sufficiently high percentage of cells of the desired cell type, and found on a sufficiently low percentage of cells of an undesired cell type. One can achieve a desired level of purification of the desired cell type from a population of cells comprising both desired and undesired cell types by selecting for cells in the population of cells that have the marker. A marker can be displayed on, for example, 30%, 35%, 40%, 45%, 50%, 55%, 60%, 65%, 70%, 75%, 80%, 85%, 90%, 95%, 99% or more of the desired cell type, and can be displayed on fewer than 50%, 45%, 40%, 35%, 30%, 25%, 20%, 15%, 10%, 5%, 1% or fewer of an undesired cell type.

In one embodiment, the disclosure provides Pgp$^+$ cells, individually or in populations. The term "isolated" or "purified" when referring to a cell(s) of the disclosure means cells that are substantially free of cells lacking the phenotypic marker (e.g., Pgp$^-$) or vice versa. In particular embodiments, the cells are at least 30%, 35%, 40%, 45%, 50%, 55%, 60%, 65%, 70%, 75%, 80%, 85%, 90%, 95% or 99% free of a contaminating cell types (e.g., Pgp$^+$ or Pgp$^-$ cells as the case may be). In another embodiment, the isolated cells also are substantially free of soluble, naturally occurring molecules. A Pgp$^+$ cell of the disclosure, for example, can be 99%-100% purified by, for example, flow cytometry (e.g., FACS analysis), as discussed herein.

In one embodiment, the disclosure provides an enriched population of Pgp$^+$ or Pgp$^-$ cells (depending upon the desired selection criteria). An "enriched population of cells" is one wherein a desired cell-type of the disclosure has been partially separated from other cell types, such that the resulting population of cells has a greater concentration of Pgp$^+$ or Pgp$^-$ cells than the original population of cells (they type of desired cell with depend upon whether you are selecting "for" or "against" Pgp expression). The enriched population of cells can have greater than about a 1.5-fold, 2-fold, 10-fold, 100-fold, 500-fold, 1,000-fold, 2,000-fold, 3,000-fold, 4,000-fold, 5,000-fold, 6,000-fold, 7,000-fold, 8,000-fold, 9,000-fold, 10,000-fold or greater concentration of, e.g., Pgp$^+$ cells than the original population had prior to separation. Pgp$^+$ cells of the disclosure can, for example, make up at least 5%, 10%, 15%, 20%, 35%, 30%, 35%, 40%, 45%, 50%, 55%, 60%, 65%, 70%, 75%, 80%, 85%, 90%, 95%, 99% or more of the enriched population of stem cells. The enriched population of cells may be obtained by, for example, selecting against cells displaying lacking a Pgp marker. Alternatively, or in addition to, the enrichment for the expression of a marker, the loss of expression of a marker may also be used for enrichment. For example, lack of expression of a marker (e.g., Pgp) can be used to select cells.

In another embodiment, the disclosure uses chemotherapeutic agents to select robust lymphocyte cells. As mentioned above, Pgp is a multidrug resistance protein that pumps a broad range of substrates, including harmful substrates such as chemotherapeutics, out of cells. Thus, cells that express Pgp including high levels of Pgp are more resistant to chemotherapeutics. Accordingly, contacting a population of cells expressing various levels of Pgp with a chemotherapeutic(s) will select for those cells that have higher expression levels of Pgp compared to those with no or low level expression of Pgp.

Similarly, dyes (e.g., photosensitive dyes) can be used in a similar fashion. In this embodiment, cells that express or over express Pgp will tend to pump out (or exclude) the dye compared to cells with low or no Pgp expression. Dye-containing cells can be separate from non-dye-containing cells. Moreover, if the dye is toxic or can be photoactivatated, cells that contain the dye can be killed thus retaining the Pgp expressing cells.

The disclosure also demonstrates that exposing cells to physical stresses, such as hyperthermic conditions, can provide selection. For example, exposing lymphocytes to higher temperatures for short periods of time provides a selective advantage to cells that express or over express Pgp compared to cells that do no expression Pgp.

The disclosure also demonstrates that exposing cells to serum-starvation and growth factor-starvation conditions can provide enrichment. For example, exposing peripheral blood stem cells to serum starvation for short periods of time results in enrichment of CD34+ cells that express or coexpress Pgp.

As disclosed herein, T cells expressing Pgp have better capacity for long-term survival and ongoing effector function after adoptive transfer. Thus, in one embodiment, expression and/or activity of P-glycoprotein can be used to select lymphocytes for adoptive cellular therapy including, but not limited to, genetic modification by CAR to produce CAR-T cells, TCRs and chimeric TCRs. Since P-glycoprotein is a cell surface protein and there a number of antibodies available against it, the current disclosure provides a method of selecting lymphocytes for adoptive cell therapy based on P-glycoprotein expression. The P-glycoprotein positive cells of the disclosure can be isolated using a number of techniques known in the art, such as magnetic activated cell sorting (MACS), in addition to conventional flow sorting. These techniques have the advantage over the method proposed by Sukumar et al. in that they are quick, economical and amenable to clinical application as a number of systems for MACS are already in clinical use. For example, Miltenyi Biotech markets a system for MACS that has FDA approval and is in clinical use in several centers.

P-glycoprotein expression can also be combined with positive and negative selection of other markers (e.g., CD8, CD4, CD62L, CD44, etc.) to further enrich lymphocytes with stem-like property and/or to enrich for stem-like T cells belonging to different subsets (e.g. cytotoxic, helper, Treg, etc.) for adoptive cellular therapy.

Provided herein are methods for isolating cells suitable for adoptive cell therapy. In one embodiment the methods comprise obtaining a sample, enriching the sample for T cells, mononuclear cells, NK cells, and/or stem cells and isolating p-glycoprotein positive (Pgp$^+$) T cells, mononuclear cells, NK cells and/or stem cells from the enriched sample, so as to obtain a fraction enriched in Pgp$^+$ T cells, NK cells, and/or stem cells suitable for adoptive cell transfer therapy. In some embodiments, the step of enriching the sample for T cells, mononuclear cells, NK cells and/or stem cells can be omitted. In some embodiments, isolating the Pgp$^+$ T cells, NK cells and/or stem cells from the sample comprises exposing the sample to at least one primary antibody or antibody-like moiety specific to p-glycoprotein. In some embodiments, the at least one primary antibody or antibody-like moiety is conjugated to at least one fluorescent label or at least one magnetic label. In some embodiments, the methods further comprise optionally staining the sample with at least one secondary antibody. In some embodiments, the at least one secondary antibody is conjugated to at least one fluorescent label or at least one magnetic label. In some embodiments, isolating of the Pgp$^+$ T cells, NK cells and/or stem cells from the sample is performed by any one or more methods selected from immunofluorescent methods, immunomagnetic methods, immunoaffinity methods or combinations thereof. In some embodiments, isolating of the Pgp$^+$ T cells, NK cells and/or stem cells from the sample is performed by any one or more methods selected from flow cytometry, magnetic activated cell sorting, biotin-streptavidin based affinity purification or combinations thereof. In some embodiments, Pgp+ T cells, NK cells and/or stem cells can be isolated from a sample (e.g. blood, bone marrow, leukopheresis sample, or peripheral blood mononuclear cells) in a single step by simultaneous labeling with fluorochrome-conjugated antibodies against Pgp and other cellular markers associated with the cell type (e.g., T cell marker(s) such as CD3) followed by sorting for Pgp+/marker² (e.g., followed by sorting for Pgp+/CD3+ T cells) by flow sorting. In some embodiments, Pgp+ T cell subsets can be isolated from a sample (e.g. blood, bone marrow, leukopheresis sample, or peripheral blood mononuclear cells) in a single step by simultaneous labeling with fluorochrome-conjugated antibodies against Pgp and T cell subset marker(s) (e.g. CD4, CD8, etc.) followed by sorting for Pgp+/CD4+ or Pgp+/CD8+ T cells by flow sorting.

In addition to separation of Pgp expressing cells based on surface labeling with Pgp antibodies, the disclosure provides methods of isolation/purification/enrichment of lymphocytes for adoptive cellular therapy based on Pgp activity. A number of cytotoxic drugs, such as Vincristine, vinblastin, doxorubicin, daunorubicin, taxol, paclitaxol, etoposide, mitoxantrone, actinomycin-D, etc. are substrates of Pgp. Therefore, Pgp-expressing cells can be enriched by exposing T cells to appropriate concentration of the above drugs that will kill Pgp-negative cells, thus isolating/purifying/enriching Pgp+ cells.

In another embodiment, the disclosure provides a method for isolating cells suitable for adoptive cell therapy, comprising obtaining a sample, enriching the sample for T cells, contacting the sample with at least one cytotoxic drug at a concentration appropriate to kill Pgp− T cells, and isolating Pgp+ T cells from the enriched sample, so as to isolate cells suitable for adoptive cell transfer therapy. In another embodiment, the disclosure provides a method for isolating cells suitable for adoptive cell therapy, comprising obtaining a sample, enriching the sample for mononuclear cells, contacting the sample with at least one cytotoxic drug at a concentration appropriate to kill Pgp-mononuclear cells, and isolating Pgp+ mononuclear cells from the enriched sample, so as to isolate cells suitable for adoptive cell transfer therapy. In some embodiments, the step of enriching the sample for T cells or mononuclear cells can be omitted prior to contain the cells with a cytotoxic drug. In some embodiments, the cytotoxic drugs are any one or more of vincristine, vinblastin, doxorubicin, or taxol, or combinations thereof. In any of the foregoing embodiments, the cell population enriched for Pgp+ cells can be further processed using antibodies to markers on the cells (e.g., anti-Pgp antibodies), dyes, or hyperthermic conditions. In some embodiments, isolating the Pgp+ T cells from the sample comprises exposing the sample to at least one primary antibody or antibody like moiety specific to p-glycoprotein. In some embodiments, the at least one primary antibody or antibody like moiety is conjugated to at least one fluorescent label or at least one magnetic label. In some embodiments, the methods further comprise optionally staining the sample with at least one secondary antibody. In some embodiments, the at least one secondary antibody is conjugated to at least one fluorescent label or at least one magnetic label. In some embodiments, isolating of the Pgp+ T cells from the sample is performed by any one or more methods selected from immunofluorescent methods, immunomagnetic methods, or combinations thereof. In some embodiments, isolating of the Pgp-positive T cells from the sample is performed by any one or more methods selected from flow cytometry, magnetic activated cell sorting, or combinations thereof.

In addition, Pgp expressing cells can be purified/enriched/isolated using photodynamic dye treatment. For example, Pgp expression cells can be purified/enriched/isolated with rhodamine analogs that are differentially retained between Pgp+ and Pgp− cells and become phototoxic on exposure to visible light. This method can be used alone or in combination with other methods of selection described herein. Exemplary rhodamine and rhodamine derivatives are known and include, for example, derivatives selected from the group consisting of 4,5-dibromorhodamine 123 (2-(4,5-dibromo-6-amino-3-imino-3H-xanthen-9-yl)-benzoic acid methyl ester hydrochloride); 4,5-dibromorhodamine 123 (2-(4,5-dibromo-6-amino-3-imino-3H-xanthen-9-yl)-benzoic acid ethyl ester hydrochloride); 4,5-dibromorhodamine 123 (2-(4,5-dibromo-6-amino-3-imino-3H-xanthen-9-yl)-benzoic acid octyl ester hydrochloride); 4,5-dibromorhodamine 110 n-butyl ester (2-(4,5-dibromo-6-amino-3-imino-3H-xanthen-9-yl)-benzoic acid n-butyl ester hydrochloride); Rhodamine B n-butyl ester (2-(6-ethyl amino-3-ethyl imino-3H-xanthen-9-yl)-benzoic acid n-butyl ester hydrochloride); and photoactivable derivatives thereof; whereby photoactivation of said derivatives induces cell killing while unactivated derivatives are substantially non-toxic to cells. Other phototoxic compounds that are substrate of Pgp have been described in the literature as well and can be used in the method of the current disclosure. For example, using a rhodamine or rhodamine analog, a population of cells can be contacted with a rhodamine or rhodamine analog under sufficient concentrations and time that allow for cells to take up the rhodamine or rhodamine analog. As described herein and above, Pgp expressing cells will pump the rhodamine or rhodamine analog out of the cell, while Pgp− or cells having reduced Pgp expression will retain the rhodamine or rhodamine analog. The population is then contacted with a light of a wavelength that causes ablation of cells containing the rhodamine or rhodamine analog (i.e., cells lacking or having reduced Pgp expression). Thus, the population will be enriched for Pgp+ cells by photo-ablation of Pgp− cells.

Due to the specific retention of the rhodamine 123 (Rh123) class of dyes by Pgp− cells and the concomitant lack of their accumulation by the lymphocytes with stem-like phenotype (e.g., by Pgp+), the disclosure provides a method for the use of these dyes for in vivo or in vitro photodynamic therapy to enrich lymphocytes for adoptive cell therapy.

Since low staining with TMRM, Rh123 and DiOC2(3) correlates with and/or is primarily due to Pgp mediated efflux and is not solely due to low mitochondrial membrane potential, the disclosure teaches an optimized protocol for isolation of Pgp expressing cells by optimizing Pgp mediated efflux. For example, by performing the assay at 37° C. and by allowing more time for Pgp mediated efflux of the dyes, a better differentiation can be obtained between Pgp+ and Pgp− cells for the purpose of adoptive cellular therapy.

In another embodiment, the disclosure provides a method for isolating cells suitable for adoptive cell therapy, comprising obtaining a sample, enriching the sample for T cells, NK cells, stem cells, and/or mononuclear cells, contacting the sample with at least one phototoxic compound, exposing the sample to a visible light source sufficient to activate the at least one phototoxic compound so as to kill Pgp− T cells, NK cells, stem cells, and/or mononuclear cells, and isolating Pgp+ T cells, NK cells, stem cells, and/or mononuclear cells from the enriched sample, so as to isolate cells suitable for adoptive cell transfer therapy. This method can be used alone or in combination with other methods for Pgp+ cell enrichment. In some embodiments, the step of enriching the sample for T cells, NK cells, stem cells, and/or mononuclear cells can be omitted. In some embodiments, the phototoxic compounds are any one or more of 2-(4,5-dibromo-6-amino-3-imino-3H-xanthen-9-yl)-benzoic acid methyl ester hydrochloride, 2-(4,5-dibromo-6-amino-3-imino-3H-xanthen-9-yl)-benzoic acid ethyl ester hydrochloride, 2-(4,5-dibromo-6-amino-3-imino-3H-xanthen-9-yl)-benzoic acid octyl ester hydrochloride, 2-(4,5-dibromo-6-amino-3-imino-3H-xanthen-9-yl)-benzoic acid n-butyl ester hydrochloride, 2-(6-ethyl amino-3-ethyl imino-3H-xanthen-9-yl)-benzoic acid n-butyl ester hydrochloride, or derivatives thereof or combinations thereof. For example, using a phototoxic, a population of cells can be contacted with a phototoxic compound under sufficient concentrations and time that allow for cells to take up the phototoxic compound. As described herein and above, Pgp expressing cells will pump the phototoxic compound out of the cell, while Pgp$^-$ or cells having reduced Pgp expression will retain the phototoxic compound. The population is then contacted with a light of a wavelength that causes ablation of cells containing the phototoxic compound (i.e., cells lacking or having reduced Pgp expression). Thus, the population will be enriched for Pgp$^+$ cells by photoablation of Pgp$^-$ cells.

In another embodiment, physical methods, such as temperature exposure, can be used to select for CD34$^+$ and/or Pgp$^+$ cells. In this embodiment, the disclosure provides a method for isolating cells suitable for adoptive cell therapy, comprising obtaining a sample, enriching the sample for T cells, NK cells, stem cells, and/or mononuclear cells, culturing the cells and exposing the population of cells to hyperthermia so as to kill Pgp$^-$ T cells, NK cells, stem cells, and/or mononuclear cells, and isolating/enriching for Pgp$^+$ T cells, NK cells, stem cells, and/or mononuclear cells. In one embodiment, the cells are exposed to a temperature from about 40-42° C. for 2-4 hours. In one embodiment, the temperature is 42-43° C. In another embodiment, the temperature is 42° C. for 2-3 hours. In another embodiment, the temperature is 43° C. for 2-3 hours. This method can be used alone or in combination with other methods for Pgp$^+$ cell enrichment. In some embodiments, the step of enriching the sample for T cells, NK cells, stem cells, and/or mononuclear cells can be omitted. For example, using a hyperthermic temperature during culturing, a population of cells can be enriched for Pgp$^+$ cells.

In another embodiment, temperature exposure can be used to select for Pgp$^+$/CD34$^+$ cells. In this embodiment, the disclosure provides a method for isolating cells suitable for adoptive cell therapy, comprising obtaining a sample, enriching the sample for T cells or mononuclear cells, culturing the cells and exposing the population of cells to hyperthermia so as to kill Pgp$^-$ T, NK or mononuclear cells, and isolating/enriching for Pgp$^+$ stem cells and mononuclear cells. In one embodiment, the cells are exposed to a temperature from about 40-42° C. for 2-4 hours. In one embodiment, the temperature is 42-43° C. In another embodiment, the temperature is 42° C. for 2-3 hours. In another embodiment, the temperature is 43° C. for 2-3 hours. The cells can then be "panned" for CD34$^+$ marker. This method can be used alone or in combination with other methods for Pgp$^+$/CD34$^+$ cell enrichment. For example, using a hyperthermic temperature during culturing, a population of cells can be enriched for Pgp$^+$/CD34$^+$ cells.

In some embodiments, where cytotoxic agents are used (e.g., chemotherapeutics and/or photoactive dyes and/or other agents) and/or physical stress (such as hyperthermic treatment) and/or nutritional/metabolic stress (e.g., serum- or growth factor starvation/depletion) are used for isolating the Pgp$^+$ cells from the sample the method can further include, after or prior to the above methods, exposing the sample to at least one primary antibody or antibody like moiety specific to p-glycoprotein. In some embodiments, the at least one primary antibody or antibody like moiety is conjugated to at least one fluorescent label or at least one magnetic label or biotin. In some embodiments, the methods further comprise optionally staining the sample with at least one secondary antibody. In some embodiments, the at least one secondary antibody is conjugated to at least one fluorescent label or at least one magnetic label or biotin. In some embodiments, isolating of the Pgp$^+$ T cells from the sample is performed by any one or more methods selected from immunofluorescent methods, immunomagnetic methods, immunoaffinity methods or combinations thereof. In some embodiments, isolating of the Pgp$^+$ T cells from the sample is performed by any one or more methods selected from flow cytometry, magnetic activated cell sorting, biotin-streptavidin based cell sorting or combinations thereof. Although not necessary, but using a combination of purification methods the enrichment of Pgp$^+$ cells can be further improved and/or optimized. In some embodiments, the fraction enriched in Pgp$^+$ T cells contains less than 50% Pgp$^-$ T cells. In some embodiments, the fraction enriched in Pgp$^+$ T cells contains less than 40% Pgp$^-$ T cells. In some embodiments, the fraction enriched in Pgp$^+$ T cells contains less than 30% Pgp$^-$ T cells. In some embodiments, the fraction enriched in Pgp$^+$ T cells contains less than 20% Pgp$^-$ T cells. In some embodiments, the fraction enriched in Pgp$^+$ T cells contains less than 10% Pgp$^-$ T cells. In some embodiments, the fraction enriched in Pgp$^+$ T cells contains less than 5% Pgp$^-$ T cells. In some embodiments, the fraction enriched in Pgp$^+$ T cells contains less than 1% Pgp$^-$ T cells.

In some embodiments, the fraction enriched in Pgp$^+$ mononuclear cells contains less than 50% Pgp$^-$ mononuclear cells. In some embodiments, the fraction enriched in Pgp$^+$ mononuclear cells contains less than 40% Pgp$^-$ mononuclear cells. In some embodiments, the fraction enriched in Pgp$^+$ mononuclear cells contains less than 30% Pgp$^-$ mononuclear cells. In some embodiments, the fraction enriched in Pgp$^+$ mononuclear cells contains less than 20% Pgp$^-$ mononuclear cells. In some embodiments, the fraction enriched in Pgp$^+$ mononuclear cells contains less than 10% Pgp$^-$ mononuclear cells. In some embodiments, the fraction enriched in Pgp$^+$ mononuclear cells contains less than 5% Pgp$^-$ mononuclear cells. In some embodiments, the fraction enriched in Pgp$^+$ mononuclear cells contains less than 1% Pgp$^-$ mononuclear cells.

In addition to Pgp, a number of other drug transporters (including breast cancer resistance protein) are selectively expressed on the surface of stem cells. Antibodies and substrates of these proteins can be also used to enrich lymphocytes with stem like phenotype for the purpose of adoptive cellular therapies. Thus, using selection techniques for these markers in combination with the selection techniques described herein for Pgp$^+$ cell can improve cell-selection processing techniques.

Once the Pgp expressing cells have been enriched by any of the above methods, the cells can be used for gene modification with CAR, TCR, chimeric TCR, synthetic immune receptor, TRuC™ T cell platform, Artemis™ T cell platform or other methods for the purpose of adoptive cellular therapy. They could be also used without gene modification, for example for immunization with T cell antigens. In some embodiments, the Pgp$^+$ T cells obtained by the methods described herein are genetically modified for use in adoptive cell therapy. In exemplary embodiments, the Pgp+ T cells are genetically modified to express at least one chimeric antigen receptor, T cell receptor, chimeric T cell receptor, synthetic immune receptor, TRuC™ T cell platform, Artemis™ T cell platform for therapeutic uses, such as for treating cancer.

In some embodiments, the genetically modified Pgp+ T cells according to any of the methods disclosed herein may be used in treating cancer, infection or immune disorders. Accordingly, in various embodiments, the disclosure provides methods for treating cancer or immune disorders in a subject, comprising providing genetically modified Pgp+ cells described herein, and administering a therapeutically effective amount of the cells to the subject so as to treat cancer.

In some embodiments, the cancer is B-cell lymphomas, T cell lymphoma, skin cancer, testicular cancer, endocrine cancer, cancer of unknown primary site, rectal cancer, anal cancer, esophageal cancer, brain tumor (e.g., glioblastoma multiforme), breast cancer, colon cancer, lung cancer, hepatocellular cancer, gastric cancer, pancreatic cancer, cervical cancer, ovarian cancer, liver cancer, bladder cancer, cancer of the urinary tract, cancer of reproductive tract, thyroid cancer, renal cancer, carcinoma, melanoma, head and neck cancer, brain cancer, prostate cancer, or leukemia. In some embodiments, the cancer is B-cell lymphomas, T cell lymphomas, myeloma, myelodysplastic syndrome, skin cancer, brain tumor, breast cancer, colon cancer, rectal cancer, esophageal cancer, anal cancer, cancer of unknown primary site, endocrine cancer, testicular cancer, lung cancer, hepatocellular cancer, gastric cancer, pancreatic cancer, cervical cancer, ovarian cancer, liver cancer, bladder cancer, cancer of the urinary tract, cancer of reproductive organs, thyroid cancer, renal cancer, carcinoma, melanoma, head and neck cancer, brain cancer, prostate cancer, or leukemia.

In some embodiments, the genetically modified Pgp+ cells described herein are administered simultaneously or sequentially with a chemotherapeutic agent. In some embodiments, the chemotherapeutic agent is selected from alkylating agents, alkyl sulfonates, aziridines, ethylenimines, methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, nitrosureas, antibiotics, dynemicin, bisphosphonates, an esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin, deoxydoxorubicin, epirubicin, esorubicin, idarubicin, marcellomycin, mitomycins, antimetabolites, folic acid analogues, purine analogs, pyrimidine analogs, androgens, anti-adrenals, folic acid replenisher, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, sizofuran, spirogermanium, tenuazonic acid, triaziquone, 2,2',2"-trichlorotriethylamine, trichothecenes, urethane, vindesine, dacarbazine, mannomustine, mitobronitol, mitolactol, pipobroman, gacytosine, arabinoside, cyclophosphamide, thiotepa, taxoids, chloranbucil, 6-thioguanine, mercaptopurine, methotrexate, platinum analogs, vinblastine, platinum, etoposide (VP-16), ifosfamide, mitoxantrone, vincristine, vinorelbine, novantrone, teniposide, edatrexate, daunomycin, aminopterin, xeloda, ibandronate, irinotecan, topoisomerase inhibitor RFS 2000; difluoromethylornithine, retinoids, capecitabine, combretastatin, leucovorin, oxaliplatin, lapatinib, inhibitors of PKC-alpha, Raf, H-Ras, EGFR and VEGF-A that reduce cell proliferation, and pharmaceutically acceptable salts, acids or derivatives of any of the above, or combinations thereof.

In addition to enriching Pgp-expressing immune cells for the purpose of adoptive T cell therapies, the disclosure also teaches methods to deplete Pgp-expressing immune cells from stem cell grafts given to patients undergoing allogeneic stem cell transplant to lower the risk of Graft versus Host disease. The disclosure also teaches methods to deplete Pgp-expressing immune cells from donor T cell given to immunodeficient patients to boost their immunity against infections while lowering the risk of Graft-vs-Host Disease (GVHD). One of skill in the art would recognize that methods described herein for killing or ablation of Pgp− cells (i.e., the selective killing of Pgp−) would not be useful for depleting a sample of Pgp+ cells. Rather methods that are capable of selectively killing or removing Pgp+ cells while leaving the Pgp-cells intact would be used.

Graft-versus-host disease (GVHD) is the main cause of mortality and a major limitation to the early and widespread use of allogeneic stem cell transplantation (SCT), a treatment that often represents the only curative option for numerous patients with malignant diseases and hereditary metabolic disorders. Depletion of T cells capable of recognizing and mounting an immune response toward host cells from stem cell grafts can reduce or even eliminate GVHD. However, the elimination of T cells also results in delayed T-cell reconstitution and, thus, an increased rate of infection, particularly with viral agents such as cytomegalovirus, herpes zoster, and Epstein-Barr virus. In addition, the eradication of mature T cells is associated with an increased risk of graft rejection and an increased incidence of relapse of malignant disease. Thus, T cells are required early after allogeneic transplantation and depleting the graft of its T-cell content is not an ideal approach to prevention of complications after transplantation. Although new immunosuppressive agents offer options to decrease the incidence and severity of GVHD, most of the time these strategies are only partially effective and may also increase the incidence of viral and fungal infections and other adverse effects of profound immunosuppression.

To provide a solution to this problem, selective inactivation or elimination of alloreactive donor T lymphocytes could allow early immune recovery and response toward infectious agents, and potentially preserve graft-versus-leukemia (GVL) activity. In addition, a strategy to selectively eliminate immunoreactive T cells could represent an important advance for the treatment of a large number of patients with autoimmune disorders. In this procedure, stimulation of T cells with mitogens or allogeneic major histocompatibility complex-mismatched cells resulted in the preferential retention of the TH9402 rhodamine-derivative in activated T cells, both CD4 and CD8. Photodynamic cell therapy of TH9402-exposed T cells led to the selective elimination of immunoreactive T-cell populations.

Based on the discovery that Pgp is expressed on T stem cells and its expression is lost upon T cell activation, Pgp− cells in a donor have been already exposed to an antigen. The likely antigens for such Pgp− cells in a healthy donor are likely to be common pathogens, such as viruses and fungi.

Thus, Pgp⁻ cells may confer immunity to pathogens commonly encountered in the environment. In contrast, Pgp⁺ cells are likely to contain naïve cells that can cause GVHD when given to a donor. Therefore, elimination of Pgp⁺ cells from a graft may enrich for T cells that can confer immunity while sparing GVHD. In the present disclosure the method depletes Pgp-expressing T cells obtained from a donor. Thus, the present method involves depletion of Pgp⁺ cells. In contrast to other methods, the method of present disclosure does not involve stimulation of donor T cells with mitogen or MHC mismatched host cells. Finally, the method of the present disclosure involves depletion of Pgp expressing cells by staining with Pgp antibody or an antibody like moiety (e.g. scFv, vHH, affibody, nanobody, Fab fragment, Darpins etc.). In the method described herein, the depletion of Pgp expressing cells is achieved by staining T cells with more than 1 antibody or antibody like moieties directed against different epitopes on the extracellular domain of Pgp. Since Pgp is also expressed on normal hematopoietic stem cells, depletion of Pgp expressing cells would potentially deplete stem cells from the graft. As such, in one method of the disclosure, stem cells are first positively selected from the graft using an antibody against CD34 antigen. This can be achieved using a commercially available CD34 isolation system (Miltenyi). Subsequently, the CD34-negative flow through fraction of the graft is depleted of Pgp expressing cells by immunostaining with Pgp antibody or a cocktail of antibodies. The CD34⁺ stem cell fraction is then administered with CD34⁻/Pgp⁻ T cell fraction to the patient undergoing allogeneic bone marrow, peripheral blood stem cell, or umbilical cord stem cell transplant. The Pgp⁻ T cell fraction can also be given to the patient at a later time than CD34⁺ stem cell infusion.

Another application of the disclosure is for adoptive cellular therapy in immunodeficient patients, such as allogeneic stem cell transplant (including umbilical cord transplant) recipients, who are immunodeficient and have become infected due to poor T cell reconstitution. Administration of a T cell population that is enriched for T cells capable of conferring immunity to viral, bacterial and fungal pathogens, but have limited capacity for alloreactivity or to cause GVHD, is highly desirable in this setting. Therefore, administration of Pgp⁻ T cell population obtained from the donor (primary donor or even third party donors) to such patients will protect against infectious agents while not significantly increasing the risk of GVHD.

In one embodiment, the disclosure provides a method for isolating Pgp⁻ T cells suitable for adoptive cell transfer therapy, comprising obtaining a sample, enriching the sample for T cells, and depleting Pgp⁺ T cells from the sample, so as to obtain a fraction enriched in Pgp⁻ T cells suitable for adoptive cell transfer therapy. In some embodiments, depleting the Pgp⁺ T cells from the sample comprises exposing the sample to at least one primary antibody or antibody like moiety specific to p-glycoprotein. In some embodiments, the at least one primary antibody or antibody like moiety is conjugated to at least one fluorescent label or at least one magnetic label or biotin. In some embodiments, the methods further comprise optionally staining the sample with at least one secondary antibody. In some embodiments, the at least one secondary antibody is conjugated to at least one fluorescent label or at least one magnetic label or biotin. In some embodiments, depleting of the Pgp⁺ T cells from the sample is performed by any one or more methods selected from immunofluorescent methods, immunomagnetic methods, immunoaffinity methods or combinations thereof. In some embodiments, depleting of the Pgp⁺ T cells from the sample is performed by flow cytometry, magnetic activated cell sorting, Biotin-streptavidin based immunoaffinity cell sorting or combinations thereof. In some embodiments, the fraction enriched in Pgp⁻ T cells contains less than 50% Pgp⁺ T cells. In some embodiments, the fraction enriched in Pgp-negative T cells contains less than 40% Pgp⁺ T cells. In some embodiments, the fraction enriched in Pgp⁻ T cells contains less than 30% Pgp⁺ T cells. In some embodiments, the fraction enriched in Pgp⁻ T cells contains less than 20% Pgp⁺ T cells. In some embodiments, the fraction enriched in Pgp⁻ T cells contains less than 10% Pgp⁺ T cells. In some embodiments, the fraction enriched in Pgp⁻ T cells contains less than 5% Pgp⁺ T cells. In some embodiments, the fraction enriched in Pgp⁻ T cells contains less than 1% Pgp⁺ T cells.

In some embodiments, the disclosure provides a method for the treatment of infection in an immunodeficient HIV/AIDS subject, comprising providing a composition comprising a population of Pgp⁻ T cells isolated by the methods described herein and administering a therapeutically effective amount of the composition to the subject so as to treat the infection. The infection may be viral infection (e.g. cytomegalovirus, adenovirus or BK virus), a bacterial infection (e.g. mycobacterium, enterococcus), fungal infection (e.g. mucor or aspergillus) or protozoan infection (e.g. toxoplasmosis).

In some embodiments, the disclosure provides a method for the treatment of infection in a subject undergoing an allogeneic stem cell transplant, comprising providing a composition comprising a population of Pgp⁻ T cells isolated by the methods described herein and administering a therapeutically effective amount of the composition comprising the Pgp⁻ cells to the subject so as to treat the infection. The infection may be viral infection (e.g. cytomegalovirus, adenovirus or BK virus), a bacterial infection (e.g. mycobacterium, enterococcus), fungal infection (e.g. mucor or aspergillus) or protozoan infection (e.g. toxoplasmosis).

In some embodiments, the disclosure provides a method for reducing graft-versus-host disease in a subject undergoing an allogeneic stem cell transplant, comprising providing a composition comprising a population of Pgp⁻ T cells isolated by the methods described herein and administering a therapeutically effective amount of the composition comprising the Pgp⁻ T cells to the subject so as to reduce graft-versus-host disease. In some embodiments, the transplant is an allogeneic bone marrow transplant, an allogeneic peripheral blood stem cell transplant, a haploidentical bone marrow transplant, a haploidentical peripheral blood stem cell transplant, or an umbilical cord stem cell transplant.

In various embodiments, the disclosure provides pharmaceutical compositions comprising a population of the Pgp⁺ T cells isolated by any of the methods disclosed herein, and at least one pharmaceutically acceptable carrier. In some embodiments, the Pgp⁺ T cells are genetically modified as described herein. In some embodiments, the pharmaceutical compositions comprising the genetically modified Pgp⁺ T cells are used in cancer therapies as described herein. In some embodiments, the pharmaceutical compositions comprising the genetically modified Pgp⁺ T cells are used in the treatment of infectious and immune disorders as described herein.

In various embodiments, the disclosure provides pharmaceutical compositions comprising a population of Pgp⁻ T cells isolated by any of the methods described herein, and at least one pharmaceutically acceptable carrier. In various embodiments, the pharmaceutical compositions comprising the Pgp⁻ T cells isolated by the methods described herein are used in therapies including but not limited to reduction of graft-versus-host disease in a subject undergoing allogeneic transplant (including stem cell transplant), treatment of an infection in a subject in need thereof and/or treatment of an infection in a HIV/AIDS subject, wherein the infection may be viral infection (e.g. cytomegalovirus, adenovirus or BK virus), a bacterial infection (e.g. mycobacterium, enterococcus), fungal infection (e.g. mucor or aspergillus) or protozoan infection (e.g. toxoplasmosis).

The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the disclosure may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection. Via the parenteral route, the compositions may be in the form of solutions or suspensions for infusion or for injection. Via the enteral route, the pharmaceutical compositions can be in the form of gel capsules, syrups, suspensions, solutions, emulsions, microspheres or lipid vesicles or polymer vesicles. Typically, the compositions are administered by injection. Methods for these administrations are known to one skilled in the art. In another embodiment, the compositions can be part of a tissue delivery device or implant. In such embodiments, the cells are allowed to grow and/or exist in a biocompatible implantable structure (e.g., with in collagen matrix and the like). In another embodiment, the cells may be applied to a structure prior to implantation (e.g., a stent, balloon, valve, pump etc.).

The pharmaceutical compositions according to the disclosure can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the disclosure can also be encapsulated or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000). In one embodiment, the pharmaceutical composition comprises Pgp⁺ or Pgp⁻ cells at $1 \times 10^5$ to $1 \times 10^8$ cells/ml (or any value there between which is expressly contemplated herein). The cells may be introduced directly into the peripheral blood or deposited within other locations throughout the body, e.g., a desired tissue, or on microcarrier beads in the peritoneum. For example, $10^2$ to $10^{11}$ cells can be transplanted in a single procedure, and additional transplants can be performed as required.

Cells can be engineered using any of a variety of vectors including, but not limited to, integrating viral vectors, e.g., retroviral vectors or lentiviral vectors or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be used, since either inducible or constitutive promoters can be used in these systems to control expression of the gene of interest. Where the vector is a non-integrating vector, such vectors can be lost from cells by dilution, as desired. An example of a non-integrating vector includes Epstein-Barr virus (EBV) vector. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection. Alternatively, cells can be engineered using transfection of in vitro transcribed mRNA.

Conventional recombinant DNA techniques can be used in the methods of the disclosure. For example, conventional recombinant DNA techniques are used to introduce a desired polynucleotide into cells (e.g., polynucleotides encoding a CAR). The precise method used to introduce a polynucleotide is not critical to the disclosure. For example, physical methods for the introduction of polynucleotides into cells include microinjection and electroporation or viral gene therapy. Chemical methods such as coprecipitation with calcium phosphate and incorporation of polynucleotides into liposomes are also standard methods of introducing polynucleotides into mammalian cells. For example, DNA or RNA can be introduced using standard vectors, such as those derived from murine and avian retroviruses (see, e.g., Gluzman et al., 1988, Viral Vectors, Cold Spring Harbor Laboratory, Cold Spring Harbor, N.Y.) or lentiviral vector systems. Standard recombinant molecular biology methods are well known in the art (see, e.g., Ausubel et al., 1989, Current Protocols in Molecular Biology, John Wiley & Sons, New York), and viral vectors for gene therapy have been developed and successfully used clinically (Rosenberg, et al., 1990, N. Engl. J. Med, 323:370). Other methods, such as naked polynucleotide uptake from a matrix coated with DNA are also encompassed by the disclosure (see, for example, U.S. Pat. No. 5,962,427, which is incorporated herein by reference).

Any promoter may be used to drive the expression of the inserted gene. For example, viral promoters include but are not limited to the CMV promoter/enhancer, SV40, papillomavirus, Epstein-Barr virus, elastin gene promoter and beta-globin. If transient expression is desired, constitutive promoters are used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

The lymphocytes or progenitor lymphocytes of the disclosure can be isolated from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, healthy or diseased tissue (e.g., tumor infiltrating lymphocytes) and the like.

Although the disclosure has exemplified in various embodiments $Pgp^+$ and $Pgp^-$ T cells, the methods and compositions of the disclosure are applicable to NK cells, $Pgp^+$ hematopoietic stem cells (e.g., $CD34^+/Pgp^+$ hematopoietic stem cells) and the like. Thus, in any of the various embodiments describe herein and throughout the specification the term "T cell" can be replaced with "NK cell" or "$CD34^+$ cell" etc. One of skill in the art will recognize that $CD34^+$ cells are stem cells and thus have additional methods and compositions applications that extend beyond T cell. For example, $CD34^+$ cells can be isolated/purified using metabolic starvation, hyperthermia and/or chemotoxic compounds and used for allogeneic or autologous stem cell transplantation with or without genetic modifications to the cells.

In another embodiment, the disclosure provides methods of establishing and/or maintaining populations of cells, or the progeny thereof, as well as mixed populations comprising various cells types as well as subpopulations (e.g., $Pgp^+$ and/or $Pgp^-$). Once a culture of cells or a mixed culture of cells and/or progenitor cell (stem-like cells) is established, the population of cells is maintained and/or mitotically expanded in vitro by passage to fresh medium as cell density dictates under conditions conducive to cell proliferation and maintenance.

Once cells or desired sub-population of cells of the disclosure have been established in culture, as described above, they may be maintained or stored in cell "banks" comprising either continuous in vitro cultures of cells requiring regular transfer or cells which have been cryopreserved.

Cryopreservation of cells of the disclosure may be carried out according to known methods, such as those described in Doyle et al., (eds.), 1995, Cell & Tissue Culture: Laboratory Procedures, John Wiley & Sons, Chichester. For example, but not by way of limitation, cells may be suspended in a "freeze medium" such as, for example, culture medium further comprising 15-20% fetal bovine serum (FBS) and 10% dimethylsulfoxide (DMSO), with or without 5-10% glycerol, at a density, for example, of about $4-10 \times 10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years, though they should be checked at least every 5 years for maintenance of viability.

The cryopreserved cells of the disclosure constitute a bank of cells, portions of which can be withdrawn by thawing and then used to produce a cell culture as needed. Thawing should generally be carried out rapidly, for example, by transferring a vial from liquid nitrogen to a $37°$ C. water bath. The thawed contents of the vial should be immediately transferred under sterile conditions to a culture vessel containing an appropriate medium. It is advisable that the cells in the culture medium be adjusted to an initial density of about $1-3 \times 10^5$ cells/ml. Once in culture, the cells may be examined daily, for example, with an inverted microscope to detect cell proliferation, and subcultured, if appropriate, as soon as they reach an appropriate density.

In another embodiment, the disclosure provides cell lines of $Pgp^+$ cells. As used herein a "cell line" means a culture of cells of the disclosure, or progeny cells thereof, that can be reproduced for an extended period of time, preferably indefinitely, and which term includes, for example, cells that are cultured, cryopreserved and re-cultured following cryopreservation. As used herein a "culture" means a population of cells grown in a medium and optionally passaged accordingly.

The following examples are intended to illustrate particular embodiments and not to limit the scope of the disclosure.

EXAMPLES

Example 1

Tetramethylrhodamine methyl ester (TMRM) was purchased from Thermofisher and dissolved in DMSO. DiOC2 (3) was purchased from Life Technologies and dissolved in methanol to produce 1 mg/ml stock solution. TH9402 was synthesized by the Weill Cornell Medicine Milstein Chemistry Core Facility and dissolved in DMSO to generate 100 mM stock. Unconjugated and FITC-conjugated monoclonal antibody (MoAb) UIC2 (IgG2a) against an extracytoplasmic domain of human Pgp was obtained from Santa Cruz Biotechnology. Fluorescein isothiocyanate—(FITC)-conjugated goat antimouse IgG was from Southern Biotechnology. Buffy coat cells were obtained from healthy de-identified adult donors from the Blood Bank at Children Hospital of Los Angeles and used to isolate peripheral blood mononuclear cells (PBMC) by Ficoll-Hypaque gradient centrifugation. PBMC were either used as such or used to isolate T cells using CD3 magnetic microbeads (Miltenyi Biotech) and following the manufacturer's instructions. PBMC or isolated T cells were re-suspended in XVIVO medium (Lonza) supplanted with 10 ng/ml soluble anti-CD3, 10 ng/ml soluble anti-CD28 and 100 IU recombinant human-IL2 unless indicated otherwise. Cells were cultured at 37° C., in a 5% $CO_2$ humidified incubator, unless indicated otherwise.

Approximately 15 million PBMC cells were stained with TMRM (20 nM final concentration) in XVIVO medium for 30 min at 37° C. in the absence or presence of Reserpine (50 µl of 1 mM stock added to 5 ml of medium with cells to give final concentration of 10 µM) or cyclosporine (10 µl of 1 mM stock added to 5 ml of medium with cells; final concentration=2 µM). All subsequent steps were done with cells maintained at 4° C. in dark. Cells were centrifuged and cell pellets were blocked with 200 µl of human AB serum for 1 hr at 4° C. Cells were washed with ice cold PBS containing 1% FCS, and divided into 3 tubes. Cells in each tube were centrifuged and cell pellets incubated for approximately 2 h in dark on ice with 1) 10 µl of FITC-conjugated UIC2 (MDR-1) antibody (Santa Cruz Biotechnology; SC-73354), 2) 1 µg of unconjugated UIC2 antibody (200 µg/ml; Santa Cruz Biotechnology; SC-73354) or 3) 1 µg of unconjugated isotype control (mouse IgG2a) antibody (eBioscience; Ref 14-4732-85). Cells labeled with unconjugated UIC2 and isotype control antibody were washed twice with PBS containing 1% FCS, centrifuged and cell pellet labeled with 5 µl (2.5 µg) of FITC-conjugated Goat F(ab)2 anti-mouse IgG (H+L) human adsorbed antibody (Southern Biotechnology; Cat #1032-02). Cells were washed twice with PBS containing 1% FCS and analyzed using BD verse flow cytometer. Cell fluorescence was analyzed in lymphoid gate based on forward and side scatter, thereby focusing the analysis on peripheral blood lymphocytes (PBL).

When stained at 37° C. in the absence of P-glycoprotein inhibitors reserpine and cyclosporine, 50% to 70% of lymphocytes were found to be TMRM-dull. In contrast, only a minor population of lymphocytes were TMRM-dull when stained in the presence of reserpine and cyclosporine, suggesting that a reserpine- and cyclosporine-sensitive efflux pump is responsible for the TMRM-dull phenotype of the vast majority of lymphocytes.

In addition to P-glycoprotein, a number of other ABC transporters have been described that are capable of pumping out lipophilic drugs, including dyes. To determine if the TMRM-dull phenotype of lymphocytes correlates with P-glycoprotein expression, double staining with TMRM and FITC-conjugated UIC2 antibody was used. However, no correlation between TMRM staining and Pgp expression, as determined by staining with FITC-UIC2 was observed. The lack of correlation between TMRM staining and FITC-UIC2 could be due to low level Pgp expression in lymphocytes which was not detected by FITC-conjugated UIC2 antibody. To increase the sensitivity of Pgp detection, the above experiment was repeated by performing indirect immunofluorescence labeling with UIC2 antibody. The use of indirect labeling results in increased sensitivity as each molecule of UIC2 antibody can be potentially bound by many molecules of FITC-labeled secondary antibody. Additionally, to further improve the sensitivity of Pgp expression, the amount of secondary antibody used was increased and the incubation volume was reduced, thereby resulting in high concentration of the secondary antibody. The incubation time was also increased to 2 h. Finally, to reduce non-specific binding of the secondary antibody, $F(ab)_2$ fragment (instead of whole antibody) that had been adsorbed against human serum proteins was used. Using this optimized staining protocol, robust expression of Pgp was observed in lymphocytes. More importantly, there was a strong inverse correlation between the levels of P-gp expression, as measured by UIC2 staining, and the retention of TMRM in the lymphocytes, indicating that the dye efflux was directly correlated with P-gp expression (FIG. 1F). Fluorescence activated cell sorting (FACS) analysis was also conducted on cells that had been stained with TMRM in the presence of Pgp inhibitors (10 µM Reserpine and 2 µM cyclosporine) and then stained with UIC2 followed by FITC conjugated Goat antimouse IgG. A vast majority of Pgp-expressing cells stained brightly with TMRM under these conditions (FIG. 1H, 1I, 1K, 1L). These results demonstrate that (i) Pgp expression has a major influence on TMRM staining of PBL; and (ii) metabolic state, as measured by mitochondrial membrane potential, is not the only determinant of TMRM staining.

Example 2. Using Immunofluorescence Staining to Enrich for Pgp Expressing Cells

Peripheral blood mononuclear cells (10 million cells) were stained as described in the previous example except three monoclonal antibodies against Pgp, including UIC2, MRK16, and 4E3 are used as primary antibodies (each at a concentration of 0.5 µg/million cells) to increase the sensitivity of the assay. Following extensive staining, cells were stained with FITC conjugated 5 µl (2.5 µg) of FITC-conjugated Goat F(ab)2 anti-mouse IgG (H+L) human adsorbed antibody (Southern Biotechnology; Cat #1032-02). Cells were washed and free antibody binding sites were blocked by addition of mouse IgG. After 2 washes, cells were labeled with PE-conjugated human CD8 antibody and APC-conjugated CD4 antibody for 1 h at 4° C. Cells were analyzed by Flow cytometry and sorted into different fractions (e.g $Pgp^+$, $Pgp^+/CD8^+$, $Pgp^+/CD4^+$, $Pgp^+/CD8^-$, $Pgp^+/CD4^-$, $Pgp^-/CD8^+$, $Pgp^-/CD4^-$).

Example 3. Using MACS (Magnetic Activated Cell Sorting) to Enrich for Pgp Expressing Cells Protocol 1. The following protocol was used to enrich Pgp expressing cells by MACS on staining with Pgp specific monoclonal antibodies and Goat anti-mouse IgG2a+IgG2b magnetic beads (Miltenyi). The blood samples to isolate peripheral blood mononuclear cells (PBMCs) were obtained from healthy de-identified adult donors. PBMC were isolated from buffy coats by Ficoll-Hypaque gradient centrifugation. Approximately 50 million PBMCs growing in XVIVO medium supplemented with hIL2 were stained with TMRM (20 nM) for 30 min at 37° C. Cells were centrifuged and cell pellet blocked with 500 µl of human serum for 1 hour at 4° C. TMRM-stained 50 million cells were separated into 3 tubes as follows: Tube 1: Stained with Pgp-UIC2 (unconjugated) antibody (1 µg/1 million cells) from Santa Cruz Biotech; Tube 2: stained with an Pgp-4E3 antibody (1 µg/1 million cells) from Abcam; Tube 3: stained with both UIC2 and 4E3 antibodies each at 1 µg/1 million cells. Cells were incubated with the above antibodies for 2 hours at 4°

C. 2 ml of MACS buffer was added to each tube, cells were centrifuged at 300× g for 10 min at 4° C. and resuspended in 80 µl MACS buffer/tube. 20 µl of anti-Mouse IgG2a+b microbeads (Miltenyi: 130-047-201) were added to each tube and cells incubated at 4° C. for 30 min. 2 ml of MACS buffer was added to each tube, cells centrifuged and resuspended into 500 µl MACS buffer. Cells were loaded cells on pre-washed MS columns (Miltenyi). Flow-through fraction was collected as negative cell fraction and column-bound cells were eluted as MDR1$^+$ (Pgp$^+$) cells following manufacturer's instructions. Aliquots of the positive and negative cells were analyzed by flow cytometer.

The results showed that there was enrichment for TMRM-dull cells (representing Pgp expressing cells) in the cells isolated based on UIC2 and 4E3 staining alone. More importantly, there was greater enrichment for TMRM-dull cells among the cells isolated based on simultaneous staining with both UIC2 and 4E3. The above results demonstrated that TMRM-dull cells can be purified based on staining with Pgp-specific antibodies that bind to the extracellular domain of Pgp. Furthermore, combination of Pgp specific antibodies, particularly those that bind to different epitopes of Pgp, can be used to obtain higher yield and greater purity. In addition to UIC2 and 4E3, a number of other Pgp antibodies are commercially available (e.g. MRK16, REA495) and can be used either alone or in combination to purify Pgp expressing (TMRM-dull) cells for the purpose of cellular therapies. Polyclonal antibodies against the extracellular domain of Pgp can be also used for the purpose of this disclosure. A rabbit polyclonal against human MDR1 protein is available from Bioss Inc. Finally, other Pgp binding moieties, such as scFv, single domain antibodies, F(ab)2 fragments, affibodies, nanobodies etc., can be used for the purpose of this invention. These antibodies (monoclonal and polyclonal) and antibody like moieties, singly or in combination, can be also used to deplete Pgp-expressing cells from a starting cell population for the purpose of cell therapies where it is desirable to deplete Pgp-expressing cells, such as to reduce Graft vs host disease in patients undergoing allogeneic stem cell transplant.

Example 4. Purification of Pgp Expressing Cells from Peripheral Blood Mononuclear Cells Using MACS Protocol 2. To enhance the purity and yield of Pgp expressing cells, the procedure in the preceding example is repeated using a cocktail of monoclonal antibodies against Pgp including UIC2, 4E3, REA495 and MRK16. Each antibody is used at 0.5 µg/million cells. Staining with primary antibodies is carried out at 4° C. for 1 h and after extensive washes the cells are incubated with 50 µl of anti-Mouse IgG beads/million cells for 2-4 hr with intermittent shaking. Positive and negative fractions are isolated as described in the previous section. The modified procedure is shown to result in greater yield and purity of Pgp-expressing cells.

Example 5. Purification of Pgp Expressing Cells from Peripheral Blood Mononuclear Cells Using MACS Protocol 3. Biotinylated REA495 antibody against Pgp and streptavidin microbeads were purchased from Miltenyi Biotech. PBMC or T cells is labeled with Biotinylated REA495 at 4° C. for 1 h following manufacturer's recommendation. After extensive washes with labeling buffer (Miltenyi Biotech), the cells are resuspended in 90 µl of labeling buffer per 10$^7$ cells. Then, 40 µl of streptavidin microbeads are added to the cells. Cells are mixed and refrigerated at 4-8° C. for 1-2 hr with intermittent shaking. Cells are washed with 1-2 ml of buffer and centrifuged at 300 g for 10 min at 4-8° C. Cells are resuspended in 500 µl of separation buffer and used for magnetic separation following the recommendations of the manufacturer. Positive and negative fractions are isolated as described in the previous section.

Example 6. Purification of Pgp Expressing Cells from T Cells Using MACs

Protocol 4. In the preceding examples, Pgp expressing cells were isolated from Peripheral blood mononuclear cells (PBMC) that were obtained from Ficoll-Hypaque separation. To purify Pgp expressing T cells, PBMC are enriched for T cells using a Pan T cell Isolation kit (Catalog #130-096-535) available from Miltenyi and following the manufacturer's recommendations. This kit uses a cocktail of antibodies against markers that are not present on T cells to deplete cells belonging to other lineages. Similar kits are available from other sources as well. The T cell enriched fraction is then positively selected for Pgp expressing cells using the protocol 1, 2 or protocol 3 described above.

Example 7. Purification of Pgp Expressing Cells from PBMC Using Photodynamic Cell Therapy with TH9402

T cells were isolated using PAN T-cell isolation kit (Miltenyi cat no. 130-096-535) from buffy coat preparation following Ficoll-Hypaque separation and RBC lysis as described above. 12 million T cells were resuspended at 1 million cells/ml in XVIVO T cell medium (Lonza) supplemented with 5 ng/ml IL7. Half (6 million) of the T cells were left untreated while the remaining half were treated with 10 µM of TH9402 compound. Cells were incubated at 37° C. in a water bath in dark for 40 min, washed with T-cell medium and then resuspended in TH9402-free T-cell medium. Cells were allowed to efflux TH9402 at 37° C. in dark in 10 ml of T cell medium for 2 h. Cells were centrifuged and re-suspended in fresh medium. Each sample was then plated in 2 wells of two different 6-well plates. One plate was left unexposed to light and the second plate was exposed for 1 h to light (1000×10 Lux units) from an LED lamp. Alternatively, light treatment can be achieved by exposure to a fluorescent light-scanning device (PDCT-Xerox Series 4, Theratechnologies) delivering 5 J/cm$^2$ at wavelength of 514 nm. After light exposure, cells were incubated in the XVIVO T cell medium with 5 ng/ml IL7 at 37° C. for 2 days in a 5% CO$_2$ incubator. After 2 days, an aliquot of the cells were stained at 4° C. for 40 min with DiOC2(3) (60 ng/ml) in 10 ml RPMI with 10% FBS medium. DiOC2(3) is a known substrate of Pgp. Cells were centrifuged, washed, resuspended in 10 ml of dye-free RPMI-10% FBS medium to efflux dye at 37° C. for 90 min. After Dye efflux, the cells were stained with Propidium iodide (PI) and examined by flow cytometry. The percentage of cells in the lymphoid gate in the various treatment groups are shown in the following table. The results show that even in the group which was untreated with TH904, there is significant enrichment for P-glycoprotein expressing lymphoid cells that stain dull with DiOC2(3) upon exposure to light (12% vs 62%), suggesting that light exposure, by itself, can lead to enrichment of Pgp-expressing T lymphocytes. Furthermore, in the group that was treated with the TH9402 compound and then exposed to light, there was further enrichment for Pgp-expressing T cells (from 10% to 80%).

Essentially similar results were obtained when the experiment was repeated with PBMC rather than purified T cells.

| Sample | % live cells (P1) | % Pgp+ cells (DiOC2 (3)-dull) |
|---|---|---|
| T-Untreated (UT)-unexposed | 75 | 12 |
| T-TH9402-treated-unexposed | 78 | 10 |
| T-UT-1 h exposure to light | 21 | 62 |
| T-TH9402-1 h exposure to light | 10 | 80 |

After 6 days, 250 µl cell aliquot from T cells were stained with DiOC2(3), allowed to efflux the dye and then stained with CD62L-APC, a marker present on human memory stem T cells ($T_{SCM}$) with stem like properties.

| Sample | % live cells (P1) | % Pgp+ (DiOC2 (3)-dull cells (based on dye efflux) (gated on live cells) | % Pgp+ (DiOC2(3)-dull) CD62L+ cells (gated on live cells) |
|---|---|---|---|
| T-UT-unexposed | 77 | 5 | 3 |
| T-TH-unexposed | 75 | 4 | 2 |
| T-UT-1 h exposure to light | 24 | 6 | 3 |
| T-TH9402-1 h exposure to light | 14 | 70 | 69 |

Figure 2:
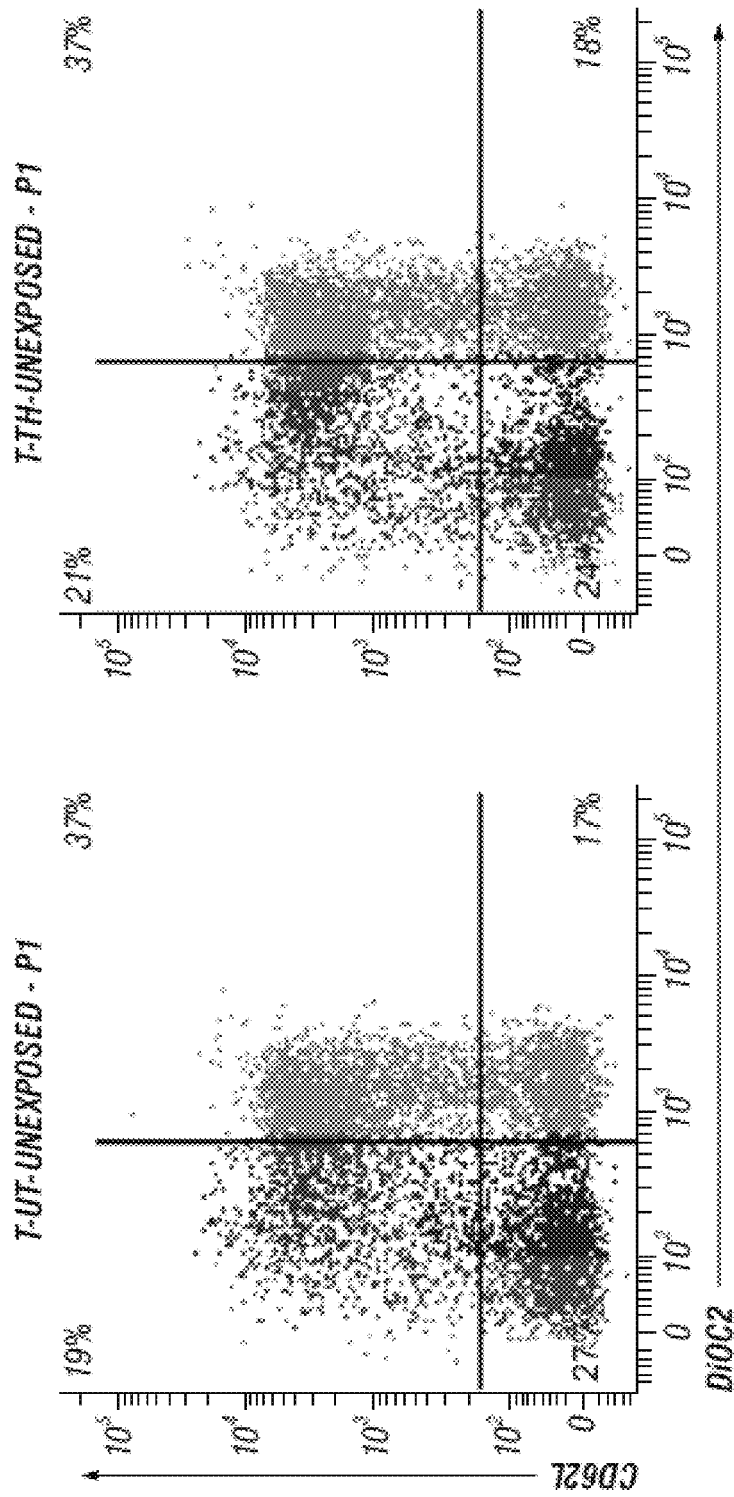
FIG. 2 shows a decline in cell viability following exposure to light in both TH9402-treated compared to non-treated cells.
Figure 2:
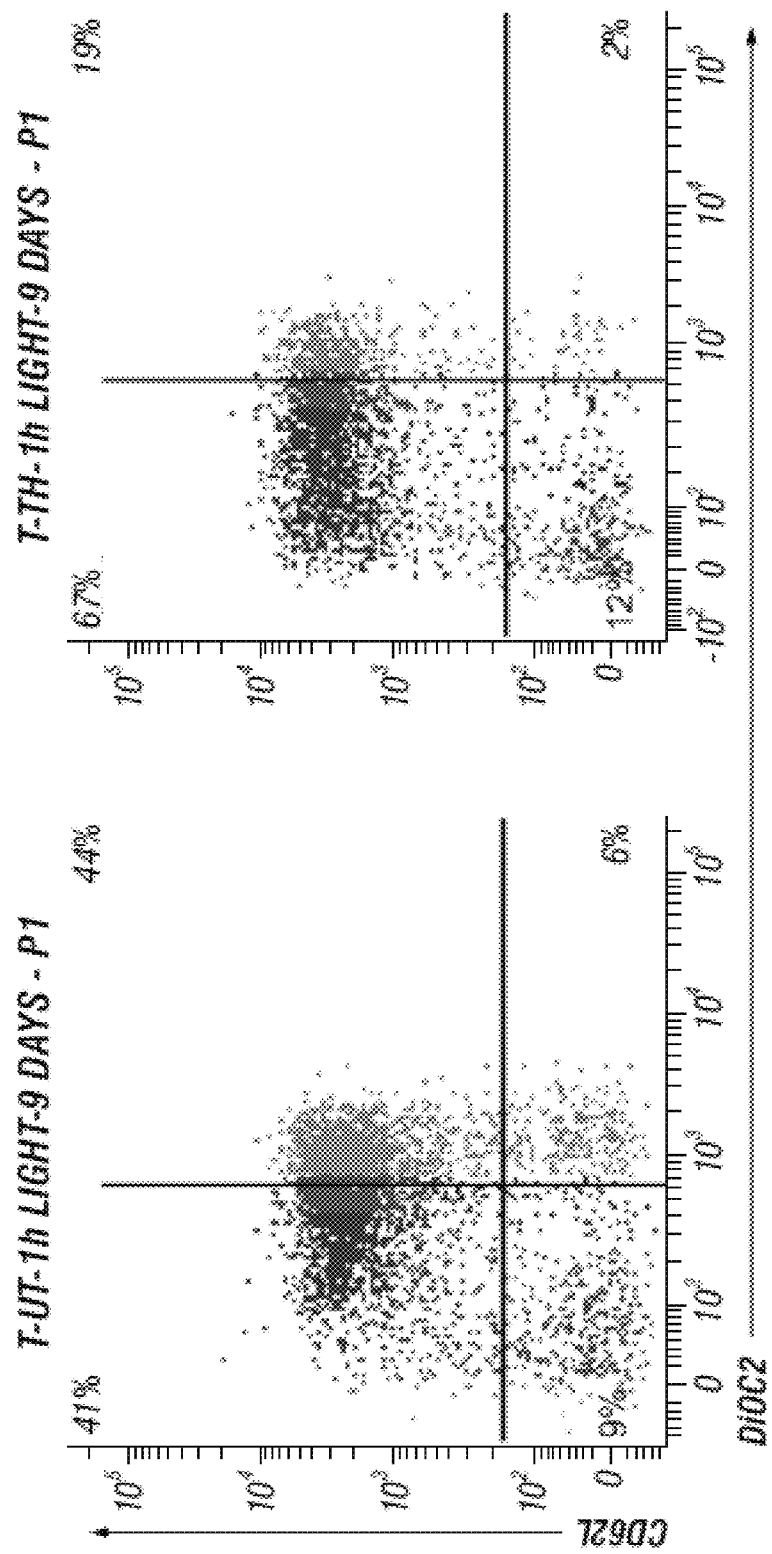

After 9 days, 1 ml cell aliquot from T cells were stained with DiOC2(3), allowed to efflux the dye and then stained with CD62L-APC, a marker present on human memory stem T cells ($T_{SCM}$) with stem like properties. Cells were then analyzed by flow cytometry. The % of cells in the different fractions are shown in FIG. 2 and the following table which show there is a significant decline in cell viability following exposure to light in both TH9402-treated and untreated cells. However, among the live cells that had been treated with TH9402 and then exposed to light, there is a significant enrichment (from 45% to 79%) for cells that express Pgp (i.e. that are DiOC2(3)-dull) as compared to cells that had not been treated with TH9402 but were then exposed to light. Furthermore, among the live cells that had been treated with TH9402 and then exposed to light, there is a significant enrichment (from 21% to 67%) for cells that express both Pgp (i.e. that are DiOC2(3)-dull) and CD62L as compared to cells that had not been treated with TH9402 but were then exposed to light.

| Sample | % live cells (Propidium iodide negative) | % Pgp+ (DiOC2 (3)-dull cells (Based on dye efflux) (gated on live cells) | % Pgp+ (DiOC2 (3)-dull), CD62L+ cells (gated on live cells) |
|---|---|---|---|
| T-UT-unexposed | 75 | 46 | 19 |
| T-TH9402-unexposed | 79 | 45 | 21 |
| T-UT-1 h exposure to light | 38 | 50 | 49 |
| T-TH9402-1 h exposure to light | 27 | 79 | 67 |

Example 9. Sorting of Pgp+ Cells, Expression of CAR in Sorted Cells

T Cells were isolated form donor blood. PBMC were isoalted after RBC lysis and Ficoll gradient. 130 million T cells were isolated from 400 million PBMCs using T-PAN isolation kit, cat no. 130-096-535 from Miltenyi. T cells were cultured in XVIVO medium with IL2 100 IU/ml. CD3 or CD28 antibodies were not added.

100 million T cells were washed with PBS+1% hAB serum at 4° C. and blocked with 500 µl hAB serum at 4° C. for 1 h followed by washing (2 times). Mixture of two primary antibodies to stain (Pgp+) MDR+ cells were used: MDR (UIC2) sc-73354 0.5 µg per million cells and P-glycoprotein antibody from Abcam, Ab 10333 0.2 µg per million cells, were used and incubated at 4° C. for 1 h followed by washing twice at 4° C.

Secondary antibody Goat F(ab')$_2$-a-mouse-IgG(H+L) human ads-FITC cat no 1032-02, Southern Biotech is prepared as a stock 0.5 mg/ml. For 100 million T cells, 250 µl of secondary antibody was added to cell pellets re-suspended in residual wash buffer, no extra buffer added. The pellets were stained for 2 hours, with intermittent shaking at 4° C., followed with two washings. The cells were re-suspended in PBS with 1 µg/ml Propidium Iodide (PI) to exclude dead cells. Cells were checked on flow for FITC staining before sorting.

Cells were sorted on a MoFlo machine. Dead, PI+, cells were excluded and FITC+ and FITC− cells collected. 9 million FITC+ cells and 7.5 million FITC− cells were collected, cultured in 6 well plates with complete T cells medium supplemented with IL2 (100 IU/ml), and CD3 (30 ng/ml) and CD28 (30 ng/ml) antibodies.

Pgp+ and Pgp− cells were infected with FMC63-BBz-A13 CAR virus, by infection three times on three days using Polybrene at 18 µl per well. Spinfection was performed at 2800 rpm, 32° C. for 90 min, and the medium was replaced with fresh medium after 6 h of infection.

Cells were expanded without selection with puromycin in IL2, CD3, and CD28 containing T cell medium. MDR+ sorted cells formed bigger clumps as compared to MDR− cells. Thus showing that Pgp+ cells proliferate more compared to Pgp− cells

| Sample | Total cell count-4 days | Total cell count-6 days | Total cell count-8 days |
|---|---|---|---|
| Pgp+ sorted-FMC63-BBz-A13 | 7 million | 12.2 million | 12 million |
| Pgp− sorted FMC63-BBz-A13 | 1.26 million cells | 0.42 million | 0 million |

Example 9. Purification of Pgp Expressing Cells by Chemotherapeutic Selection Criteria T cells were isolated using CD3 microbeads. Cells were resuspended in T cell culture medium and treated under the following conditions.
1. High dose Vincristine Treatment: Cells were treated with Vincristine (Sigma) at doses of 100, 250, 500, 750, 1000 ng/ml for 24 h. The following day, the medium was changed and cells cultured in Vincristine-free medium.
2. Intermediate Dose Vincristine Treatment: Cells were treated with vincristine at intermediate doses of 5, 10, 20, 30, 50 ng/ml with continuous exposure of the drug thereafter.
3. Low dose Vincristine Treatment: Cells were treated with vincristine at low doses 0.5, 1, 2, 2.5, 3 ng/ml with continuous exposure to the drug thereafter.
4. Cells were treated with Akt inhibitor vIII (Cat #124018, Calbiochem), at 1 µM final conc.
5. Cells were treated with Etoposide at dose 100, 500, 1000 nM
6. Cells were treated with Adriamycin (doxorubicin) at 0.1, 0.5, 1 µg/ml T cells treated with intermediate and high dose of vincristine were checked for Pgp$^+$ enrichment by DiOC2(3) efflux assay and cell death by Propidium iodide staining after 2 days of treatment. Cells were analyzed by flow cytometry. The results as shown in the table below demonstrate a modest enrichment of Pgp$^+$ cells with higher dose vincristine treatments after 2 days.

| Samples: 2 days post-treatment | % Cell Death (PI+ cells) | % Pgp$^+$ (DiOC2(3)-dull) (out of live cells) |
|---|---|---|
| Untreated | 14 | 8 |
| Vincristine-5 ng/ml | 13 | 8 |
| Vincristine-10 ng/ml | 15 | 9 |
| Vincristine-20 ng/ml | 15 | 9 |
| Vincristine-30 ng/ml | 20 | 11 |
| Vincristine-50 ng/ml | 15 | 10 |
| Vincristine-100 ng/ml | 28 | 11 |
| Vincristine-250 ng/ml | 31 | 11 |
| Vincristine-500 ng/ml | 27 | 13 |
| Vincristine-750 ng/ml | 30 | 14 |
| Vincristine-1 µg/ml | 31 | 14 |

T cells treated with low, intermediate and high dose of vincristine were checked for Pgp$^+$ enrichment by DiOC2(3) efflux assay and cell death by Propidium iodide staining after 2 days of treatment and after 7 days of treatment. The results are shown in the following table and demonstrate that after 7 days of vincristine treatment, there was a significant enrichment of Pp cells with 1 µg/ml Vincristine from 5% in untreated group to 18% in the 1 µg/ml-treated group.

| Samples: 7 days post-treatment | % Cell Death (PI+ cells) | % Pgp+ (DiOC2(3)-dull) (gated on live cells) |
|---|---|---|
| UT | 9 | 5 |
| Vincristine-0.5 ng/ml | 10 | 7 |
| Vincristine-1 ng/ml | 12 | 7 |
| Vincristine-2 ng/ml | 8 | 7 |
| Vincristine-2.5 ng/ml | 10 | 7 |
| Vincristine-3 ng/ml | 14 | 9 |
| Vincristine-5 ng/ml | 9 | 8 |
| Vincristine-10 ng/ml | 9 | 10 |
| Vincristine-20 ng/ml | 9 | 10 |
| Vincristine-50 ng/ml | 14 | 9 |
| Vincristine-100 ng/ml | 16 | 13 |
| Vincristine-250 ng/ml | 25 | 11 |
| Vincristine-500 ng/ml | 26 | 9 |
| Vincristine-750 ng/ml | 29 | 10 |
| Vincristine-1 µg/ml | 23 | 18 |

T cells treated with drugs other than vincristine were checked for Pgp$^+$ enrichment after 8 days of treatment using the assay described above. Treatment with adrimycin (doxorubicin) at 1 µg/ml showed significant enrichment of Pgp$^+$ or DiOC2(3)-dull cells.

| Sample (8 days post-treatment) | % Cell Death (PI+ cells) | % pgp+ (out of live cells) |
|---|---|---|
| UT | 3 | 16 |
| Rapamycin-100 ng/ml | 11 | 15 |
| RAD1001-0.2 ng/ml | 7 | 15 |
| RAD1001-1 ng/ml | 5 | 15 |
| Adriamycin-0.1 µg/ml | 5 | 16 |
| Adriamycin-0.5 µg/ml | 7 | 16 |
| Adriamycin-1 µg/ml | 12 | 27 |
| Etoposide-0.1 uM | 5 | 15 |
| Etoposide-0.5 unM | 4 | 16 |
| Etoposide-1 uM | 5 | 15 |
| Akt-inhibitor-1 uM | 4 | 19 |
| Verapamil-1 uM | 4 | 17 |
| Verapamil-5 uM | 3 | 17 |
| Verapamil-10 uM | 3 | 17 |

Example 10. Temperature Selection of Pgp-Expression Cells

T cells were isolated as described above. Three different water baths were set up at 42, 43 and 44° C. Four 6-well plates labelled as 37, 42, 43 and 44 containing 1 ml of T-cell medium were kept at 37° C. incubator to pre-warm the media. T cells (1 million cells/ml) in 1 ml of T-cell medium with IL7 (5 ng/ml) were kept at 37° C. or in the above water baths for the indicated time intervals as follows:
1. 37° C.
2. 42° C. for 1 h
3. 42° C. for 2 h
4. 42° C. for 3 h
5. 42° C. for 4 h
6. 42° C. for 5 h
7. 42° C. for 6 h
8. 43° C. for 1 h
9. 43° C. for 2 h
10. 43° C. for 3 h
11. 43° C. for 4 h
12. 43° C. for 5 h
13. 43° C. for 6 h
14. 44° C. for 1 h
15. 44° C. for 2 h
16. 44° C. for 3 h
17. 44° C. for 4 h
18. 44° C. for 5 h
19. 44° C. for 6 h After each time point, cells were added to separate wells of 6 well plates containing the pre-warmed medium and kept at 37° C. for rest of the experiment.

After 5 days the percentage of Pgp⁺ cells were checked by DiOC2(3) efflux to check if exposure of T cells to high temperature for short time point can enrich Pgp⁺ cell population. The results are shown in the following Table and demonstrate significant enrichment of Pgp⁺ (DiOC2(3)-dull) cells following exposure to elevated temperatures. For example, DiOC2(3)-dull cells showed enrichment from 76% to 98% when exposed to 43° C. for 2 hours as compared to cells kept at 37° C.

| Sample | Live cells (%) | Pgp+ (DIOC2-effluxing cells (gated on live cells) |
|---|---|---|
| T-37° C. | 65 | 76 |
| T-42° C.-1 h | 62 | 77 |
| T-42° C.-2 h | 67 | 96 |
| T-42° C.-3 h | 50 | 93 |
| T-43° C.-1 h | 60 | 93 |
| T-43° C.-2 h | 20 | 98 |
| T-43° C.-3 h | 4 | 95 |

Peripheral blood stem cell cells were obtained from a patient undergoing stem cell transplantation. Cells underwent RBC lysis to get rid of red cells and Ficoll-Hypaque separation to enrich for mononuclear cells. Approximately, 10 million cells were recovered and approximately 7 million cells were used for hyperthermia experiment. Cells were resuspended in 15 ml Falcon tubes at approximately 1 million cells/ml and were kept at 37° C. or in a water-bath at 43° C. for the indicated time intervals as follows:

37° C.
43° C. for 0.5 h
43° C. for 1 h
43° C. for 1.5 h
43° C. for 2 h
43° C. for 2.5 h
43° C. for 3 h Following exposure cells were transferred to a 6 well plate at incubated at 37° C. in Stem-cell medium XVIVO-10 supplemented with SCF, TPO, FLT3, IL3, IL6 (all at 50 ng/ml) in a humidified 5% CO₂ incubated for 72 h. 100 μl aliquots were then stained with 1 μg/ml Propidium iodide to check cell death.

| Sample | % lymphocytes (P1 population) | % PI+ve dead cells |
|---|---|---|
| T-37° C. | 18 | 12 |
| T-43° C.-0.5 h | 16 | 13 |
| T-43° C.-1 h | 8 | 23 |
| T-43° C.-1.5 h | 6 | 31 |
| T-43° C.-2 h | 7 | 29 |
| T-43° C.-2.5 h | 5 | 39 |
| T-43° C.-3 h | 5 | 36 |

After 96 hours, cells were stained with DiOC2(3) (60 ng/ml in 5 ml of RPMI 10% FBS medium at 4° C. for 40 min). The cells were washed with medium, dye-efflux in 10 ml RPMi 10% medium at 37° C. for 90 min, washed twice with PBS 1% FBS, and stained with 1.5 μl/sample/100 μl of CD34-APCefluor 780 (ebiosciences cat #470349-42) at 4° C. for 1 h. The cells were washed and analyzed by Flow Cytometry. APC-efluor-780 was detected in APC-Cy7 channel in BD Facsverse. The results demonstrate significant enrichment of Pgp⁺ cells from 48% to 76-80% following exposure to 43° C. for different time intervals. In addition there is enrichment of Pgp⁺/CD34⁺ stem cells from 1% to 2% in cells exposed to 43° C. for 3 h as compared to cells cultured at 37° C.

| Sample | % Pgp⁺ (DiOC2-effluxing cells) | % Pgp⁺CD34⁺ |
|---|---|---|
| T-37° C. | 48 | 1 |
| T-43° C.-0.5 h | 76 | 0.3 |
| T-43° C.-1 h | 70 | 1 |
| T-43° C.-1.5 h | 76 | 0.5 |
| T-43° C.-2 h | 76 | 1 |
| T-43° C.-2.5 h | 76 | 0.5 |
| T-43° C.-3 h | 80 | 2 |

Example 11. Use of Pgp Enriched Cells for Adoptive Cellular Therapy

The blood samples to isolate peripheral blood mononuclear cells (PBMCs) are obtained from healthy de-identified adult donors. PBMC are isolated from buffy coats by Ficoll-Hypaque gradient centrifugation. Pgp expressing cells are purified from PBMC by any one or more of the methods described in the previous examples, including Flow sorting, MACS and photodynamic cell therapy with TH9402, selection with vincristine and hyperthermia. Pgp⁺ T cells, Pgp⁻ T cells and unpurified T cells are re-suspended in XVIVO medium (Lonza) supplanted with 10 ng/ml soluble anti-CD3, 10 ng/ml soluble anti-CD28 and 100 IU recombinant human-IL2. Cells are engineered to express FMC63(vL-vH)-Myc-BBz-PAC Chimeric Antigen Receptor (CAR) targeting human CD19 by infection with pLENTI-EF1a-FMC63(vL-vH)-Myc-BBz-T2A-Pac-A13 lentiviral vector. NSG mice (Jackson Lab) are sub-lethally irradiated at a dose of 175 cGy. 24 hours post irradiation (day 2), mice are injected with 2.5×10⁴ RAJI cells via tail-vein. On day 3, the mice (n=5 for each group) are injected by tail vein with 1 million Pgp⁺, Pgp⁻, or unpurified T cells that had been infected with the FMC63(vL-vH)-Myc-BBz-PAC lentivirus. Control mice (n=5) are injected with RAJI cells but do not receive T cells. Survival of mice injected with Pgp⁺ CAR-T cells is significantly higher than those of mice injected with Pgp⁻ CAR-T cells or unpurified T cells. This is true irrespective of the method (flow sorting, MACS or TH9402 plus light exposure, selection with vincristine or hyperthermia) used to purify Pgp⁺ cells. PCR analysis for the presence of CAR-modified T cells in blood and bone marrow reveals longer in vivo persistence of CAR-T cells that are derived from Pgp⁺ cells.

The above experiment is repeated using Pgp⁺/CD8⁺, Pgp⁻/CD8⁺, Pgp⁺/CD4⁺, Pgp⁺/CD4⁻ starting population of cells. Again, CAR generated from Pgp+ve cells perform better than those generated from Pgp⁻ cells and persisted longer in vivo.

Example 12. Use of Autologous Pgp-Expressing Cells for Adoptive Cell Therapy Patients with relapsed Acute lymphocytic Leukemia (ALL) or high-risk intermediate grade B-cell lymphomas may receive immunotherapy with adoptively transferred autologous Pgp⁺ T cells-derived CAR-T cells. A leukapheresis product collected from each patient undergoes selection of Pgp⁺ T cells using Flow sorting with Pgp antibodies, MACS using Pgp antibodies, Photodynamic selection following exposure to TH9402 plus light, selection with vincristine or hyperthermia. Cells are transduced with clinical grade CD19CAR virus and then selection and expansion of the CAR-T cells occur in a closed system. After the resulting cell products have undergone quality control testing (including sterility and tumor specific cytotoxicity tests), they are cryopreserved. Meanwhile, following leukapheresis, study participants commence with lymphodepletive chemotherapy following which they receive their cryopreserved CAR-T cells. The CAR-T cell product is transported, thawed and infused at the patient's bedside. The dose of CAR-T product varies from $1 \times 10^4$ CAR$^+$ CD3 cells/kg to $1 \times 10^9$ CAR$^+$ CD3 cells/kg as per the study protocol. The CAR product may be administered in a single infusion or split infusions. Research participants can be pre-medicated at least 30 minutes prior to T cell infusion with 15 mg/kg of acetaminophen P.O. (max. 650 mg) and diphenhydramine 0.5-1 mg/kg I.V. (max dose 50 mg). Clinical and laboratory correlative follow-up studies can then be performed at the physician's discretion, and may include quantitative RT-PCR studies for the presence of CD19-expressing ALL/lymphoma cells and/or the adoptively transferred T cells; FDG-PET and/or CT scans; bone marrow examination for disease specific pathologic evaluation; lymph node biopsy; and/or long-term follow up per the guidelines set forth by the FDA's Biologic Response Modifiers Advisory Committee that apply to gene transfer studies.

Example 13. Use of Allogeneic Pgp-Expressing Cells for Adoptive Cells Therapy

Patients with relapsed Acute Lymphocytic Leukemia (ALL) or high-risk intermediate grade B-cell lymphomas who have undergone an allogeneic bone marrow transplant may receive immunotherapy with adoptively transferred allogeneic Pgp$^+$ T cells-derived CAR-T cells. A leukapheresis product collected from the donor (same donor as used for the allogeneic transplant) undergoes selection of Pgp$^+$ T cells using Flow sorting following staining with Pgp antibodies, MACS following staining with Pgp antibodies, Photodynamic selection following exposure to TH9402 plus light, selection with vincristine or hyperthermia. Cells are transduced with clinical grade CD19-CAR and then selection and expansion of the CAR-T cells occur in a closed system. After the resulting cell products have undergone quality control testing (including sterility and tumor specific cytotoxicity tests), they are cryopreserved. Meanwhile, study participants commence with lymphodepletive chemotherapy following which they receive the cryopreserved allogeneic CAR-T cells. The CAR-T cell product is transported, thawed and infused at the patient's bedside. The dose of CAR-T product may vary from $1 \times 10^4$ CAR$^+$ CD3 cells/kg to $1 \times 10^9$ CAR$^+$ CD3 cells/kg as per the study protocol. The CAR product may be administered in a single infusion or split infusions. Research participants can be pre-medicated at least 30 minutes prior to T cell infusion with 15 mg/kg of acetaminophen P.O. (max. 650 mg) and diphenhydramine 0.5-1 mg/kg I.V. (max dose 50 mg). Clinical and laboratory correlative follow-up studies can then be performed at the physician's discretion, and may include quantitative RT-PCR studies for the presence of CD19-expressing ALL/lymphoma cells and/or the adoptively transferred T cells; FDG-PET and/or CT scans; bone marrow examination for disease specific pathologic evaluation; lymph node biopsy; and/or long-term follow up per the guidelines set forth by the FDA's Biologic Response Modifiers Advisory Committee that apply to gene transfer studies. Use of immunosuppressive drugs is also at the discretion of the physician.

Example 14. Use of Pgp Negative T Cells to Reduce the Incidence of GVHD in Patients Undergoing Allogeneic Bone Marrow Transplant and Other Disorders Peripheral blood stem cells are obtained from a donor using leukopheresis following standard procedures. The donor may be, for example, an HLA-matched (10/10 match) sibling donor, 10/10 matched unrelated donor, or Antigen mismatched sibling or unrelated donor, or a haploidentical donor. The leukopheresed product is enriched for CD34-expressing cells by positive selection using the CliniMACS Prodigy® System from Miltenyi Biotec and following the manufacturer's recommendations. The CD34$^-$ fraction is labeled with one or more antibodies against extracellular domain of Pgp (e.g. UIC2, 4E3, MRK16 etc.) followed by incubation with Goat anti-mouse IgG magnetic beads and negative selection using the CliniMACS Prodigy® System, and following the manufacturer's recommendations. Alternatively, negative selection for Pgp-expressing cells can be obtained by using one, or a cocktail, of Pgp antibodies that are directly conjugated to magnetic beads. The Pgp negative fraction should contain less than 50% Pgp-expressing cells, or preferably less than 40% Pgp-expressing cells, or preferably less than 30% Pgp-expressing cells, or preferably less than 20% Pgp-expressing cells, or preferably less than 10% Pgp-expressing cells, or preferably less than 5% Pgp-expressing cells, or preferably less than 1% Pgp-expressing cells. The patient who has received the conditioning regimen (myeloablative or reduced intensity or non-myeloablative) to prepare for transplant is then administered by intravenous infusion the CD34 enriched stem cell fraction along with Pgp-depleted T cell fraction. The proportion and amount of Pgp-depleted T cell fraction that is administered to the patient is at the discretion of the physician. For example, from $1 \times 10^4$ CD3 cells/kg to $1 \times 10^9$ CD3 cells/kg may be infused either as a single infusion or split infusion depending on the tolerance of the patient and discretion of the treating physician.

Example 15. Use of Pgp-Negative T Cell Product for the Treatment of CMV (Cytomegalovirus) Infection in an Allogeneic Stem Cell Transplant Recipient A patient who is status-post allogeneic stem cell transplant from an unrelated donor develops refractory CMV infection. Peripheral blood mononuclear cells are collected from the original donor, who is CMV seropositive. T cells are first enriched by negative selection using a cocktail of antibodies against non-T cell markers and using the CliniMACS Prodigy® System. The T cell fraction is then depleted of Pgp-expressing cells by incubation with a Pgp antibody or cocktail of antibodies (1-2 µg/million cells) followed by negative selection using the CliniMACS Prodigy® System, and following the manufacturer's recommendations. The Pgp-depleted fraction of T cells is administered to the patient intravenously either as a single infusion or in increasing fractions, at the discretion of the treating physician. For example, from $1 \times 10^4$ Pgp$^-$/CD3$^+$ cells/kg to $1 \times 10^9$ Pgp$^-$/CD3$^+$ cells/kg may be infused either as a single infusion or split infusion depending on the tolerance of the patient and discretion of the treating physician.

Example 16. Use of Pgp-Negative T Cell Product for the Treatment of CMV (Cytomegalovirus) Infection in an Immunodeficient HIV/AIDS Recipient A patient with HIV/AIDS develops refractory CMV infection. Peripheral blood mononuclear cells are collected from an HLA matched donor, who is CMV seropositive. T cells are first enriched by negative selection using a cocktail of antibodies against non-T cell markers and using the CliniMACS Prodigy® System. The T cell enriched fraction is then depleted of Pgp-expressing cells by incubation with a Pgp antibody or a cocktail of antibodies (1-2 µg/million cells) followed by negative selection using the CliniMACS Prodigy® System, and following the manufacturer's recommendations. The Pgp-depleted fraction of T cells is administered to the patient intravenously either as a single infusion or in increasing fractions, at the discretion of the treating physician. For example, from $1\times10^4$ Pgp$^-$/CD3$^+$ cells/kg to $1\times10^9$ Pgp$^-$/CD3$^+$ cells/kg may be infused either as a single infusion or split infusion depending on the tolerance of the patient and discretion of the treating physician.

Example 17. Use of Pgp-Negative T Cell Product for the Treatment of Adenovirus Infection in an Allogeneic Stem Cell Transplant Recipient A patient who is status-post allogeneic stem cell transplant from an unrelated donor develops refractory adenovirus infection. Peripheral blood mononuclear cells are collected from the original donor, who is adenovirus seropositive. T cells are first enriched by negative selection using a cocktail of antibodies against non-T cell markers and using the CliniMACS Prodigy® System. The T cell fraction is then depleted of Pgp-expressing cells by incubation with a Pgp antibody or cocktail of antibodies (1-2 µg/million cells) followed by negative selection using the CliniMACS Prodigy® System, and following the manufacturer's recommendations. The Pgp-depleted fraction of T cells is administered to the patient intravenously either as a single infusion or in increasing fractions, at the discretion of the treating physician. For example, from $1\times10^4$ Pgp$^-$/CD3$^+$ cells/kg to $1\times10^9$ Pgp$^-$/CD3$^+$ cells/kg may be infused either as a single infusion or split infusions depending on the tolerance of the patient and discretion of the treating physician.

Example 18. Use of Pgp-Negative T Cell Product for the Treatment of BK Virus Infection in an Allogeneic Stem Cell Transplant Recipient A patient who is status-post allogeneic stem cell transplant from an unrelated donor develops refractory BK virus infection. Peripheral blood mononuclear cells are collected from the original donor BK virus seropositive. T cells are first enriched by negative selection using a cocktail of antibodies against non-T cell markers and using the CliniMACS Prodigy® System. The T cell fraction is then depleted of Pgp-expressing cells by incubation with a Pgp antibody or cocktail of antibodies (1-2 µg/million cells) followed by negative selection using the CliniMACS Prodigy® System, and following the manufacturer's recommendations. The Pgp-depleted fraction of T cells is administered to the patient intravenously either as a single infusion or in increasing fractions, at the discretion of the treating physician. For example, from $1\times10^4$ Pgp$^-$/CD3$^+$ cells/kg to $1\times10^9$ Pgp$^-$/CD3$^+$ cells/kg may be infused either as a single infusion or split infusion depending on the tolerance of the patient and discretion of the treating physician.

Figure 3:
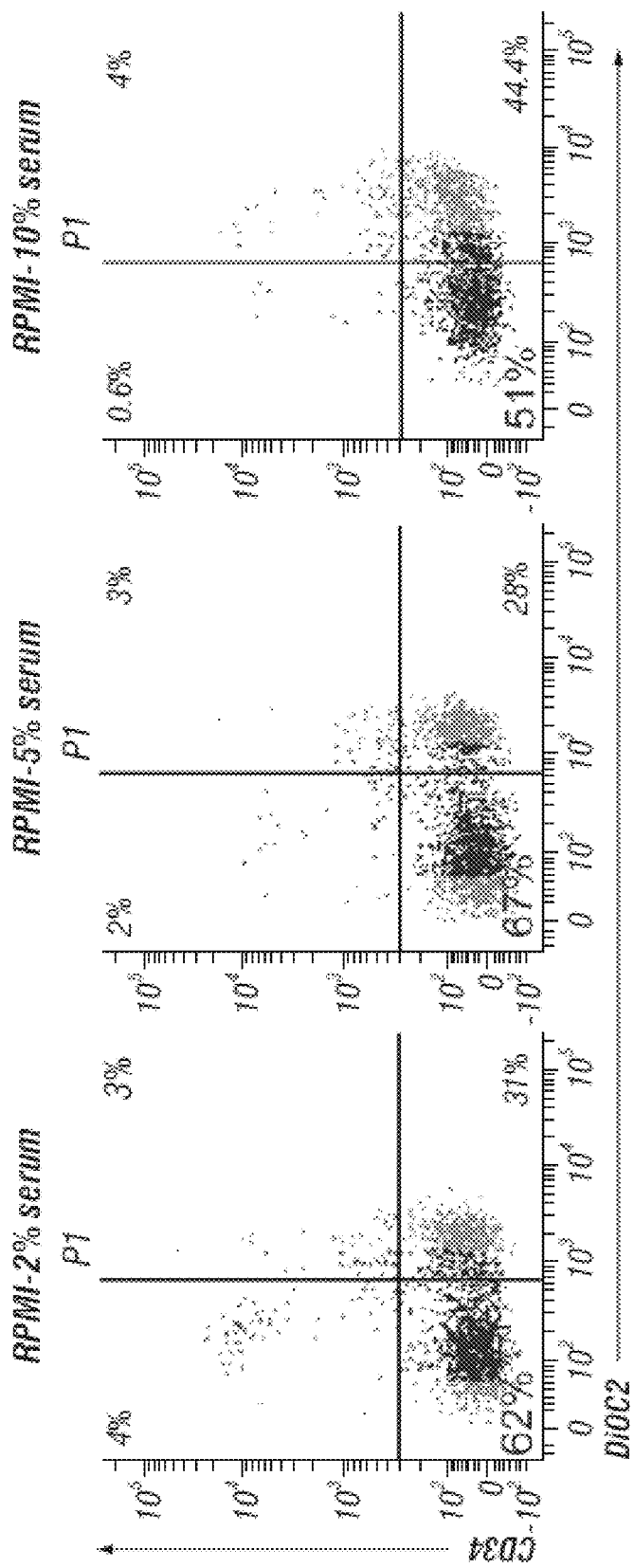
FIG. 3 shows that serum starvation results in a significant enrichment of CD34$^+$ stem cells.

Example 19. Enrichment of Pgp$^+$/CD34$^+$ Pluripotent Hematopoietic Stem Cells Using Serum-Starvation The most primitive pluripotent hematopoietic stem cells are known to co-express CD34 and Pgp and efflux DiOC2(3) (Chaudhary and Roninson, Cell, 66, 85-94, 1991). To examine if these cells can be enriched by serum starvation, peripheral blood stem cell cells were collected by apheresis from a patient undergoing stem cell transplantation after mobilization with chemotherapy and G-CSF using standard procedures for stem cell mobilization and collection. Cells underwent RBC lysis to get rid of red cells and Ficoll-Hypaque separation to enrich for mononuclear cells. Cells were cultured for 6 days in RPMI medium containing 2%, 5% or 10% Fetal bovine Serum (FBS). Cells were stained with DiOC2(3) (60 ng/ml in 5 ml of RPMI 10% FBS medium at 4° C. for 40 min). The cells were washed with medium, dye-efflux in 10 ml RPMi 10% medium at 37° C. for 90 min, washed twice with PBS 1% FBS, and stained with 1.5 µl/sample/100 µl of CD34-APCefluor 780 (ebiosciences cat #470349-42) at 4° C. for 1 h. The cells were washed and analyzed by Flow Cytometry. APC-efluor-780 was detected in APC-Cy7 channel in BD Facsverse. FIG. 3 shows significant enrichment of CD34$^+$ stem cells from 4.6% to 5% to 7% upon reduction of FBS from 10% to 5% to 2%. Furthermore, there was significant enrichment of the most primitive hematopoietic stem cells that are DiOC2(3)-dull (or Pgp$^+$) and CD34$^+$ from 0.6% to 2% to 4% upon reduction of FBS from 10% to 5% to 2%. These results demonstrate that CD34$^+$ hematopoietic stem cells and CD34$^+$/Pgp$^+$ pluripotent hematopoietic stem cells can be enriched by serum starvation.

Figure 4:
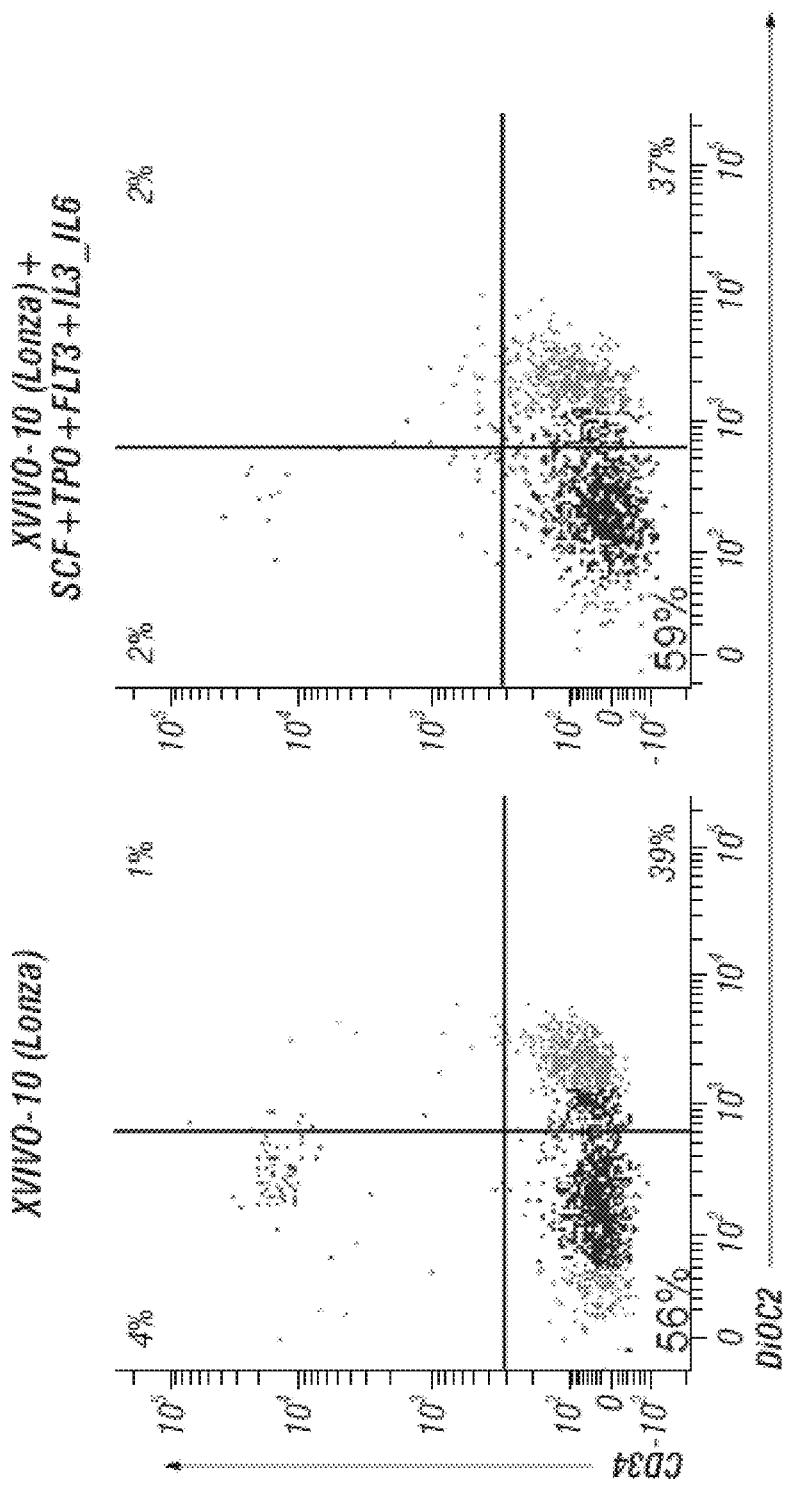
FIG. 4 shows that growth factor starvation resulted in an enrichment of CD34$^+$ cells.

Example 20. Enrichment of Pgp$^+$/CD34$^+$ Pluripotent Hematopoietic Stem Cells by Growth Factor-Starvation The experiment was conducted as in the preceding example except that cells were cultured for 6 days in XVIVO-10 (Lonza) medium alone or XVIVO-10 medium containing SCF (50 ng/ml), TPO (50 ng/ml), FLT3 (50 ng/ml), IL3 (50 ng/ml) and IL6 (50 ng/ml). There was an enrichment of CD34$^+$/DiOC2(3)-dull pluripotent hematopoietic stem cells from 2% to 4% when the cells were cultured in the medium lacking growth factors (FIG. 4).

Example 21. Use of Pgp-Positive/CD34$^+$ Cell Product for Allogeneic Stem Cell Transplantation A patient with aplastic anemia is a candidate for allogeneic bone marrow (or peripheral blood stem cell) transplant from a one antigen mismatched related donor. Bone marrow is harvested from the donor under general anesthesia. In order to reduce the incidence of graft-vs-host disease, the bone marrow is enriched for hematopoietic stem cells by positive selection for CD34$^+$ cells using CliniMACS Prodigy® System. To further enrich for the most primitive hematopoietic progenitors, the CD34$^+$ cell fraction is enriched for cells that are Pgp$^+$ by exposure to TH9402 plus light, selection with vincristine or hyperthermia. For enrichment using TH9402, cells are incubated at 37° C. with 10 µM TH9402 (Theratechnologies, Montreal, QC, Canada) in X-Vivo 15 medium with 2.5% HAB. After a 40-minute incubation, cells are centrifuged and dye efflux favored by resuspending cells in TH9402-free medium for 90 minutes. At the end of the latter dye efflux period, cells are exposed to a fluorescent light-scanning device (PDCT-Xerox Series 4, Theratechnologies) delivering 5 J/cm$^2$ at a wavelength of 514 nm. For enrichment using hyperthermia, the cells are exposed to 43° C. for 3 hours. The final CD34$^+$/Pgp$^+$ cellular product (2.5-5 million cells/Kg of body weight) is used for allogeneic transplantation after the patient has received myeloablative conditioning regimen. Patient receives standard post-allogeneic transplant care, including use of immunosuppressive drugs, under the direction of the treating physician.

Example 22. Use of Pgp-Positive/CD34+ Cell Product for Gene Therapy

A patient with X-linked severe combined immunodeficiency (SCID-X1) is a candidate for gene therapy with interleukin-2 receptor γ-chain (γc) complementary DNA. Bone marrow is harvested from the patient under general anesthesia. Bone marrow is enriched for hematopoietic stem cells by positive selection for CD34$^+$ cells using CliniMACS Prodigy® System. To further enrich for the most primitive hematopoietic progenitors, the CD34$^+$ cell fraction is enriched for cells that are Pgp$^+$ by exposure to TH9402 plus light, selection with vincristine or hyperthermia. For enrichment using TH9402, cells are incubated at 37° C. with 10 µM TH9402 (Theratechnologies, Montreal, QC, Canada) in X-Vivo 15 medium with 2.5% HAB. After a 40-minute incubation, cells are centrifuged and dye efflux favored by resuspending cells in TH9402-free medium for 90 minutes. At the end of the latter dye efflux period, cells are exposed to a fluorescent light-scanning device (PDCT-Xerox Series 4, Theratechnologies) delivering 5 J/cm$^2$ at a wavelength of 514 nm. For enrichment using hyperthermia, the cells are exposed to 42.5° C. for 3 hours. The final CD34$^+$/Pgp$^+$ cellular product (5 million cells/Kg of body weight) is used for gene transfer with a lentiviral vector encoding the γc cDNA using published regimen (Gaspar H B et al., Lancet, 2004; 364:2181-7). Patient receives infusion of approximately 5×10$^6$/Kg CD34$^+$/Pgp$^+$ gene modified stem cells without preparative conditioning. Patient showed sustained recovery of T cells, including CD3$^+$, CD8$^+$ and CD4$^+$ subsets and normal immunological function.

Example 23. Enrichment of Stem Like T Cells Using Serum-Starvation

To examine if T stem cells can be enriched by serum starvation, the experiment in example 19 is repeated using T cells isolated from peripheral blood. There is enrichment of the DiOC2(3)-dull (or Pgp+) cells following culture in RPMI medium containing 2% FCS as compared to RPMI medium containing 10% serum. These results demonstrate that T cells with stem like characteristic and/or Pgp$^+$ T cells can be enriched by serum starvation.

A number of embodiments have been set forth above to illustrate the invention. The following claims further set forth what the Applicants regard as their invention.

What is claimed is:

1. A method for isolating T cells and/or NK cells suitable for adoptive cell therapy, comprising:
    (a) obtaining a sample comprising T cells and/or NK cells;
    (b) optionally enriching the sample for T cells and/or NK cells; and
    (c) isolating p-glycoprotein positive (Pgp+) T cells and/or NK from the sample, so as to obtain a fraction enriched in Pgp-positive T cells and/or NK cells by
        (i) contacting the sample with at least one phototoxic compound that is a substrate of Pgp; and
        (ii) exposing the sample to a light source sufficient to activate the at least one phototoxic compound so as to kill Pgp-negative cells,
    thereby isolating T cells and/or NK cells suitable for adoptive cell transfer therapy.

2. The method of claim 1, wherein the cells are contacted with the at least one phototoxic compound for a time and at a temperature sufficient to allow efflux of the phototoxic compound.

3. The method of claim 1, wherein after contact with the at least one phototoxic compound the cells are removed from the phototoxic compound for a time and at a temperature sufficient to allow efflux of the phototoxic compound.

4. The method of claim 2, wherein the temperature is 37° C.

5. The method of claim 1, wherein the at least one phototoxic compound is any one or more of 2-(4,5-dibromo-6-amino-3-imino-3H-xanthen-9-yl)-benzoic acid methyl ester hydrochloride, 2-(4,5-dibromo-6-amino-3-imino-3H-xanthen-9-yl)-benzoic acid ethyl ester hydrochloride, 2-(4,5-dibromo-6-amino-3-imino-3H-xanthen-9-yl)-benzoic acid octyl ester hydrochloride, 2-(4,5-dibromo-6-amino-3-imino-3H-xanthen-9-yl)-benzoic acid n-butyl ester hydrochloride, 2-(6-ethyl amino-3-ethyl imino-3H-xanthen-9-yl)-benzoic acid n-butyl ester hydrochloride, or derivatives thereof or combinations thereof.

6. The method of claim 1, wherein the light source is a visible light source.

7. The method of claim 1, wherein the Pgp+ cells are further enriched using other methods for Pgp enrichment.

8. The method of claims 1, wherein the fraction enriched in Pgp+ cells contains less than (a) 50% Pgp− cells; b) 40% Pgp− cells; c) 30% Pgp− cells; d) 20% Pgp− cells; d) 10% Pgp− cells; e) 5% Pgp− cells; or f) 1% Pgp− n cells.

9. The method of claim 1, wherein the Pgp+ cells are further genetically modified so as to obtain genetically modified Pgp+ cells.

10. The method of claim 9, wherein the genetically modified Pgp+ cells are selected from the group consisting of T cells and/or NK cells.

11. The method of claim 1, wherein Pgp+ T cells are further genetically modified to express at least one chimeric antigen receptor, T cell receptor, synthetic immune receptor, chimeric T cell receptor, or other genetic element so as to obtain genetically modified Pgp-positive T cells.

\* \* \* \* \*

SEQUENCE LISTING

```
Sequence total quantity: 1
SEQ ID NO: 1              moltype = DNA  length = 9659
FEATURE                   Location/Qualifiers
source                    1..9659
                          mol_type = other DNA
                          organism = synthetic construct
SEQUENCE: 1
aatgtagtct tatgcaatac tcttgtagtc ttgcaacatg gtaacgatga gttagcaaca   60
tgccttacaa ggagagaaaa agcaccgtgc atgccgattg gtggaagtaa ggtggtacga  120
tcgtgcctta ttaggaaggc aacagacggg tctgacatgg attggacgaa ccactgaatt  180
gccgcattgc agagatattg tatttaagtg cctagctcga tacataaacg ggtctctctg  240
gttagaccag atctgagcct gggagctctc tggctaacta gggaacccac tgcttaagcc  300
tcaataaagc ttgccttgag tgcttcaagt agtgtgtgcc cgtctgttgt gtgactctgg  360
taactagaga tccctcagac ccttttagtc agtgtggaaa atctctagca gtggcgcccg  420
aacagggact tgaaagcgaa agggaaacca gaggagctct ctcgacgcag gactcggctt  480
gctgaagcgc gcacggcaag aggcgagggg cggcgactgg tgagtacgcc aaaaattttg  540
actagcggag gctagaagga gagagatggg tgcgagagcg tcagtattaa gcgggggaga  600
attagatcgc gatgggaaaa aattcggtta aggccagggg gaaagaaaaa atataaatta  660
aaacatatag tatgggcaag cagggagcta gaacgattcg cagttaatcc tggcctgtta  720
gaaacatcag aaggctgtag acaaatactg ggacagctac aaccatccct tcagacagga  780
tcagaagaac ttagatcatt atataataca gtagcaaccc tctattgtgt gcatcaaagg  840
atagagataa aagacaccaa ggaagcttta gacaagatag aggaagagca aaacaaaagt  900
aagaccaccg cacagcaagc ggccgctgat cttcagacct ggaggaggag atatgaggga  960
caattggaga agtgaattat ataaatataa agtagtaaaa attgaaccat taggagtagc 1020
acccaccaag gcaaagagaa gagtggtgca gagagaaaaa agagcagtgg gaataggagc 1080
tttgttcctt gggttcttgg gagcagcagg aagcactatg ggcgcagcgt caatgacgct 1140
gacggtacag gccagacaat tattgtctgg tatagtgcag cagcagaaca atttgctgag 1200
ggctattgag gcgcaaacag atctgttgca actcacagtc tggggcatca agcagctcca 1260
ggcaagaatc ctggctgtgg aaagatacct aaaggatcaa cagctcctgg ggatttgggg 1320
ttgctctgga aaactcattt gcaccactgc tgtgccttgg aatgctagtt ggagtaataa 1380
atctctggaa cagatttgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680
tcagacccac ctcccaaccc cgaggggacc cgacaggccc gaaggaatag aagaagaagg 1740
tggagagaga gacagagaca gatccattcg attagtgaac ggatctcgac ggtatcggtt 1800
aactttttaa agaaaagggg ggattggggg gtacagtgca ggggaaagaa tagtagacat 1860
aatagcaaca gacatacaaa ctaaagaatt acaaaaacaa attacaaaat tcaaaatttt 1920
atcgataagc tttgcaaaga tggataaagt tttaaacaga gaggaatctt tgcagctaat 1980
```

```
ggaccttcta ggtcttgaaa ggagtgcctc gtgaggctcc ggtgcccgtc agtgggcaga  2040
gcgcacatcg cccacagtcc ccgagaagtt ggggggaggg gtcggcaatt gaaccggtgc  2100
ctagagaagg tggcgcgggg taaactggga aagtgatgtc gtgtactggc tccgcctttt  2160
tcccgagggt gggggagaac cgtatataag tgcagtagtc gccgtgaacg ttcttttcg  2220
caacgggttt gccgccagaa cacaggtaag tgccgtgtgt ggttcccgcg ggcctggcct  2280
ctttacgggt tatggcccmtt gcgtgccttg aattacttcc acctggctgc agtacgtgat  2340
tcttgatccc gagcttcggg ttgaagtgg gtgggagagt tcgaggcctt gcgcttaagg  2400
agcccttcg cctcgtgctt gagttgaggc ctggcctggg cgctggggcc gccgcgtgcg  2460
aatctggtgg caccttcgcg cctgtctcgc tgctttcgat aagtctctag ccatttaaaa  2520
tttttgatga cctgctgcga cgcttttttt ctggcaagat agtcttgtaa atgcgggcca  2580
agatctgcac actggtattt cggttttgg ggccgcgggc ggcgacgggg cccgtgcgtc  2640
ccagcgcaca tgttcggcga ggcggggcct gcgagcgcgg ccaccgagaa tcggacgggg  2700
gtagtctcaa gctggccggc ctgctctggt gcctggcctc gcgccgccgt gtatcgcccc  2760
gccctgggcg gcaaggctgg cccggctcggc accagttgcg tgagcggaaa gatggccgct  2820
tcccggccct gctgcaggga gctcaaaatg gaggacgcgg cgctcgggag agcgggcggg  2880
tgagtcaccc acacaaagga aaagggcctt tccgtcctca gccgtcgctt catgtgactc  2940
cacgagtac cgggcgccgt ccaggcacct cgattagttc tcgacctttt ggagtacgtc  3000
gtctttaggt tgggggagg ggtttatgc gatggagttt ccccacactg agtgggtgga  3060
gactgaagtt aggccagctt ggcacttgat gtaattctcc ttggaatttg ccctttttga  3120
gtttggatct tggttcattc tcaagcctca gacagtggtt caaagttttt ttcttccatt  3180
tcaggtgtcg tgaggaatta gcttggtact aatacgactc actatagggga gacccaagct  3240
ggctagttaa gcttgatatc gaattcctgc agcccgggggt atctgctac atggccttac  3300
cagtgaccgc cttgctcctg ccgctggcct tgctgctcca cgccgccagg ccggacatcc  3360
agatgacaca gactacatcc tccctgtctg cctctctggg agacagagtc accatcagtt  3420
gcagggcaag tcaggacatt agtaaatatt taaattggta tcagcagaaa ccagatggaa  3480
ctgttaaact cctgatctac catacatcaa gattacactc aggagtccca tcaaggttca  3540
gtggcagtgg gtctggaaca gattattctc tcaccattag caacctggag caagaagata  3600
ttgccactta cttttgccaa cagggtaata cgcttccgta cacgttcgga ggggggacca  3660
agctggagat cacaggtggc ggtggctcgg gcggtggtgg gtcgggtggc ggcggatctg  3720
aggtgaaact gcaggagtca ggacctggcc tggtggcgcc ctcacagagc ctgtccgtca  3780
catgcactgt ctcaggggtc tcattacccg actatggtgt aagctggatt cgccagcctc  3840
cacgaaaggg tctggagtgg ctgggagtaa tatgggtgtg tgaaaccaca tactataatt  3900
cagctctcaa atccagactg accatcatca aggacaactc caagagccaa gttttcttaa  3960
aaatgaacag tctgcaaact gatgacacag ccatttacta ctgtgccaaa cattattact  4020
acggtggtag ctatgctatg gactactggg gtcaaggaac ctcagtcacc gtctcctcac  4080
gcgtagagca gaaactgatc tcggaagagg atctggcgaa gccaccacg acgcagcgc  4140
cgcgaccacc aacaccggcg cccaccatcg cgtcgcagcc cctgtccctg cgcccagagg  4200
cgtgccggcc agcggcgggg ggcgcagtgc acacgagggg gctggacttc gcctgtgaca  4260
tctacatctg ggcgcccttg gccggtactt gtggggttctc tcctctgtca ctggttatca  4320
cccttactg caaacgggc agaaagaaac tcctgtatatt attcaaacaa ccatttatga  4380
gaccagtaca aactactcaa gaggaagatg gctgtagctg ccgatttcca gaagaagaag  4440
aaggaggatg tgaactgaga gtgaagttca gcaggagcgc agacgccccc gcgtaccagc  4500
agggccagaa ccagctctat aacgactgaa atctaggacg aagagaggag tacgatgttt  4560
tggacaagag acgtggccgg gaccctgaga tgggggaaaa gccgagaagg aagaaccctc  4620
aggaaggcct gtacaatgaa ctgcagaaag ataagatggc ggaggcctac agtgagattg  4680
ggatgaaagg cgagcgccgg aggggcaagg ggcacgatgg cctttaccag ggtctcagta  4740
cagccaccaa ggacacctac gacgcccttc acatgcaggc ctgcccct cgctctagtg  4800
gctccggcga gggcagagga agtctactaa cctgcggaga tgtggaagaa atcctggcc  4860
cacatatgac cgagtacaag cccacggtgc gcctcgccac ccgcgacgac gtccccaggg  4920
ccgtacgcac cctcgcccgc cgcgttcgccg actacccgc cacgcgccac accgtcgatc  4980
cggaccgcca catcgagcgg gtcaccgagc tgcaagaact cttcctcacg cgcgtcgggc  5040
tcgacatcgg caaggtgtgg gtcgcggacg acggcgccgc ggtggcggtc tggaccacgc  5100
cggagagcgt cgaagcgggg gcggtgttcg ccgagatcgg cccgcgcatg gccgagttga  5160
gcggttccg gctggccgcg cagcaacaga tggaaggcct cctggcgccg caccggccca  5220
aggagcccgc gtggttcctg gccaccgtcg gcgtctccgc cgaccaccag ggcaagggtc  5280
tgggcagcgc cgtcgtgctc ccggagtgg aggcggccga gcgcgccggg gtgcccgcct  5340
tcctggagac ctccgcgccc cgcaacctcc ccttctacga gcggctcggc ttcaccgtca  5400
ccgccgacgt cgaggtgccc gaaggaccgc gcacctggtg catgacccgc aagccggtg  5460
cctgagtcga ctccggatga tcagggccct gtacagatat cgacaatcaa cctctggatt  5520
acaaaatttg tgaaagattg actggtattc ttaactatgt tgctccttt acgctatgtg  5580
gatacgctgc tttaatgcct ttgtatcatg ctattgcttc ccgtatggct ttcattttct  5640
cctccttgta taaatcctgg ttgctgtctc tttatgagga gttgtggccc gttgtcaggc  5700
aacgtggcgt ggtgtgcact gtgtttgctg acgcaacccc cactggttgg ggcattgcca  5760
ccacctgtca gctcctttcc gggactttcg ctttccccct cctattgcc acggcggaac  5820
tcatcgccgc ctgccttgcc cgctgctgga caggggctcg gctgttgggc actgacaatt  5880
ccgtggtgtt gtcggggaag ctgacgtcct tccatggct gctcgcctgt gttgccacct  5940
ggattctgcg cggggacgtcc ttctgctacg tcccttcggc cctcaatcca gcggaccttc  6000
cttcccgcgg cctgctgccg gctctgcggc ctcttccgcgt cttcgccttt cgccctcaga  6060
cgagtcggat ctccctttgg gccgcctccc cgcctggaat tcgagtcgg taccttaag  6120
accaatgact tacaaggcag ctgtagatct tagccactt ttaaaagaaa agggggact  6180
ggaagggcta attcactccc aacgaagaca agatctgctt tttgcttgta ctgggtctct  6240
ctggttagac cagatctgag cctgggagct ctctggctaa ctagggaacc cactgcttaa  6300
gcctcaataa agcttgcctt gagtgcttca agtagtgtgt gcccgtctgt tgtgtgactc  6360
tggtaactag agatccctca gaccctttta gtcagtgtgg aaaatctcta gcagtagtag  6420
ttcatgtcat cttattattc agtatttata acttgcaaag aaatgaatat cagagagtga  6480
gaggaacttg tttattgcag cttataatgg ttacaaataa agcaatagca tcacaaattt  6540
cacaaataaa gcattttttt cactgcattc tagttgtggt ttgtccaaac tcatcaatgt  6600
atcttatcat gtctggctct agctatccg ccctaactc cgcccatccc gcccctaact  6660
ccgcccagtt ccgcccattc tccgccccat ggctgactaa ttttttttat ttatgcagag  6720
```

```
gccgaggccg cctcggcctc tgagctattc cagaagtagt gaggaggctt ttttggaggc 6780
ctagggacgt acccaattcg ccctatagtg agtcgtatta cgcgcgctca ctggccgtcg 6840
ttttacaacg tcgtgactgg gaaaaccctg gcgttaccca acttaatcgc cttgcagcac 6900
atccccctttt cgccagctgg cgtaatagcg aagaggcccg caccgatcgc ccttcccaac 6960
agttgcgcag cctgaatggc gaatgggacg cgccctgtag cggcgcatta agcgcggcgg 7020
gtgtggtggt tacgcgcagc gtgaccgcta cacttgccag cgccctagcg cccgctcctt 7080
tcgctttctt cccttccttt ctcgccacgt tcgccggctt tccccgtcaa gctctaaatc 7140
gggggctccc tttagggttc cgatttagtg ctttacggca cctcgacccc aaaaaacttg 7200
attagggtga tggttcacgt agtgggccat cgccctgata gacggttttt cgccctttga 7260
cgttggagtc cacgttcttt aatagtggac tcttgttcca aactggaaca acactcaacc 7320
ctatctcggt ctattctttt gatttataag ggattttgcc gatttcggcc tattggttaa 7380
aaaatgagct gatttaacaa aaatttaacg cgaattttaa caaaatatta acgcttacaa 7440
tttaggtggc acttttcggg gaaatgtgcg cggaaccccct atttgtttat ttttctaaat 7500
acattcaaat atgtatccgc tcatgagaca ataaccctga taaatgcttc aataatattg 7560
aaaaaggaag agtatgagta ttcaacattt ccgtgtcgcc cttattccct tttttgcggc 7620
attttgcctt cctgtttttg ctcacccaga aacgctggtg aaagtaaaag atgctgaaga 7680
tcagttgggt gcacgagtgg gttacatcga actggatctc aacagcggta agatccttga 7740
gagtttttcgc cccgaagaac gttttccaat gatgagcact tttaaagttc tgctatgtgg 7800
cgcggtatta tcccgtattg acgccgggca agagcaactc ggtcgccgca tacactattc 7860
tcagaatgac ttggttgagt actcaccagt cacagaaaag catcttacgg atggcatgac 7920
agtaagagaa ttatgcagtg ctgccataac catgagtgat aacactgcgg ccaacttact 7980
tctgacaacg atcggaggac cgaaggagct aaccgctttt ttgcacaaca tgggggatca 8040
tgtaactcgc cttgatcgtt gggaaccgga gctgaatgaa gccataccaa acgacgagcg 8100
tgacaccacg atgcctgtag caatggcaac aacgttgcgc aaactattaa ctggcgaact 8160
acttactcta gcttccggc aacaattaat agactggatg gaggcggata aagttgcagg 8220
accacttctg cgctcggccc ttccggctgg ctggtttatt gctgataaat ctggagccgg 8280
tgagcgtggg tctcgcggta tcattgcagc actggggcca gatggtaagc cctcccgtat 8340
cgtagttatc tacacgacgg ggagtcaggc aactatggat gaacgaaata gacagatcgc 8400
tgagataggt gcctcactga ttaagcattg gtaactgtca gaccaagttt actcatatat 8460
actttagatt gatttaaaac ttcatttttta atttaaaagg atctaggtga agatcctttt 8520
tgataatctc atgaccaaaa tcccttaacg tgagttttcg ttccactgag cgtcagaccc 8580
cgtagaaaag atcaaaggat cttcttgaga tcctttttttt ctgcgcgtaa tctgctgctt 8640
gcaaacaaaa aaaccaccgc taccagcggt ggtttgtttg ccggatcaag agctaccaac 8700
tcttttttccg aaggtaactg gcttcagcag agcgcagata ccaaatactg ttcttctagt 8760
gtagccgtag ttaggccacc acttcaagaa ctctgtagca ccgcctacat acctcgctct 8820
gctaatcctg ttaccagtgg ctgctgccag tggcgataag tcgtgtctta ccgggttgga 8880
ctcaagacga tagttaccgg ataaggcgca gcggtcgggc tgaacggggg gttcgtgcac 8940
acagcccagc ttggagcgaa cgacctacac cgaactgaga tacctacagc gtgagctatg 9000
agaaagcgcc acgcttcccg aagggagaaa ggcggacagg tatccggtaa gcggcagggt 9060
cggaacagga gagcgcacga gggagcttcc agggggaaac gcctggtatc tttatagtcc 9120
tgtcgggttt cgccacctct gacttgagcg tcgatttttg tgatgctcgt caggggggcg 9180
gagcctatgg aaaaacgcca gcaacgcggc ctttttacgg ttcctggcct tttgctggcc 9240
ttttgctcac atgttctttc ctgcgttatc ccctgattct gtggataacc gtattaccgc 9300
ctttgagtga gctgataccg ctcgccgcag ccgaacgacc gagcgcagcg agtcagtgag 9360
cgaggaagcg gaagagcgcc caatacgcaa accgcctctc cccgcgcgtt ggccgattca 9420
ttaatgcagc tggcacgaca ggtttcccga ctggaaagcg ggcagtgagc gcaacgcaat 9480
taatgtgagt tagctcactc attaggcacc ccaggcttta cactttatgc ttccggctcg 9540
tatgttgtgt ggaattgtga gcggataaca atttcacaca ggaaacagct atgaccatga 9600
ttacgccaag cgcgcaatta accctcacta aagggaacaa aagctggagc tgcaagctt  9659
```